US012121366B2

(12) United States Patent
Shen et al.

(10) Patent No.: US 12,121,366 B2
(45) Date of Patent: Oct. 22, 2024

(54) SENSORIZED SHOELACE-TENSIONING SYSTEM AND METHOD

(71) Applicant: The Board of Trustees of The University of Alabama, Tuscaloosa, AL (US)

(72) Inventors: Xiangrong Shen, Tuscaloosa, AL (US); Edward Sazonov, Northport, AL (US); Md Rejwanul Haque, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 112 days.

(21) Appl. No.: 17/547,369

(22) Filed: Dec. 10, 2021

(65) Prior Publication Data

US 2022/0257185 A1   Aug. 18, 2022

Related U.S. Application Data

(60) Provisional application No. 63/148,756, filed on Feb. 12, 2021.

(51) Int. Cl.
| | |
|---|---|
| G08B 21/00 | (2006.01) |
| A43C 1/00 | (2006.01) |
| A61B 5/00 | (2006.01) |
| A61B 5/11 | (2006.01) |
| G01L 5/04 | (2006.01) |

(Continued)

(52) U.S. Cl.
CPC ............ *A61B 5/6807* (2013.01); *A43C 1/003* (2013.01); *A61B 5/1117* (2013.01); *A61B 5/112* (2013.01); *A61B 5/7275* (2013.01); *A61B 5/746* (2013.01); *G01L 5/047* (2013.01);

*G01P 13/00* (2013.01); *A61B 2503/08* (2013.01); *A61B 2503/10* (2013.01); *A63B 71/0619* (2013.01); *A63B 2220/836* (2013.01); *A63B 2225/50* (2013.01)

(58) Field of Classification Search
CPC ..... A61B 5/6807; A61B 5/1117; A61B 5/112; A61B 5/7275; A61B 5/746; A61B 2503/08; A61B 2503/10; A43C 1/003; G01L 5/047; G01P 13/00; A63B 71/0619; A63B 2220/836; A63B 2225/50
USPC ........................................................ 340/668
See application file for complete search history.

(56) References Cited

U.S. PATENT DOCUMENTS 5,157,813  A  * 10/1992  Carroll ................. A43C 11/165
                                                            36/114
11,206,891 B2 * 12/2021  Beers ...................... A43B 11/00
(Continued)

FOREIGN PATENT DOCUMENTS

| CN | 105722419 A | * | 6/2016 | ............. A43B 11/00 |
| CN | 111315249 A | * | 6/2020 | ............. A43B 13/14 |

(Continued)

OTHER PUBLICATIONS

Beers, T., "Has a Removable Footwear of the Motor Adjusting System", Jun. 29, 2016, CN105722419A (Year: 2016).*

(Continued)

*Primary Examiner* — Naomi J Small
(74) *Attorney, Agent, or Firm* — Meunier Carlin & Curfman LLC

(57) ABSTRACT

The present disclosure relates to systems and devices for measuring motion of a shoe and tension in the shoelace of the shoe.

22 Claims, 29 Drawing Sheets

(51) Int. Cl.
    G01P 13/00    (2006.01)
    A63B 71/06    (2006.01)

(56) References Cited

U.S. PATENT DOCUMENTS

| | | | | |
|---|---|---|---|---|
| 11,533,967 | B2* | 12/2022 | Beers | A43C 11/00 |
| 2011/0054359 | A1 | 3/2011 | Sazonov et al. | |
| 2017/0272008 | A1* | 9/2017 | Schneider | A43C 11/008 |
| 2019/0098963 | A1* | 4/2019 | Beers | A43C 11/008 |
| 2019/0174862 | A1* | 6/2019 | Rakshit | G06F 3/016 |
| 2020/0297063 | A1* | 9/2020 | Andon | H04W 4/80 |

FOREIGN PATENT DOCUMENTS

| | | | | |
|---|---|---|---|---|
| CN | 116714728 | A * | 9/2023 | |
| FR | 3038815 | A1 * | 1/2017 | A43B 11/00 |
| TW | 202139878 | A * | 11/2021 | A43B 1/0054 |

OTHER PUBLICATIONS

MarketsandMarkets, "Wearable Technology Market worth $265.4 billion by 2026—Exclusive Report by MarketsandMarketsTM." https://www.prnewswire.com/news-releases/wearable-technology-market-worth-265-4-billion-by-2026--exclusive-report-by-marketsandmarkets-301269737.html (accessed Nov. 10, 2021).

R. Wagner and A. Ganz, "PAGAS: Portable and Accurate Gait Analysis System," Annu Int Conf IEEE Eng Med Biol Soc, vol. 2012, pp. 280-283, 2012, doi: 10.1109/EMBC.2012.6345924.

P. Lopez-Meyer, G. D. Fulk, and E. S. Sazonov, "Automatic detection of temporal gait parameters in poststroke individuals," IEEE Trans Inf Technol Biomed, vol. 15, No. 4, pp. 594-601, Jul. 2011, doi: 10.1109/TITB.2011.2112773.

S. J. M. Bamberg, A. Y. Benbasat, D. M. Scarborough, D. E. Krebs, and J. A. Paradiso, "Gait Analysis Using a Shoe-Integrated Wireless Sensor System," IEEE Transactions on Information Technology in Biomedicine, vol. 12, No. 4, pp. 413-423, Jul. 2008, doi: 10.1109/TITB.2007.899493.

B. Mariani, M. C. Jiménez, F. J. G. Vingerhoets, and K. Aminian, "On-Shoe Wearable Sensors for Gait and Turning Assessment of Patients With Parkinson's Disease," IEEE Transactions on Biomedical Engineering, vol. 60, No. 1, pp. 155-158, Jan. 2013, doi: 10.1109/TBME.2012.2227317.

S. Crea, M. Donati, S. M. M. De Rossi, C. M. Oddo, and N. Vitiello, "A Wireless Flexible Sensorized Insole for Gait Analysis," Sensors, vol. 14, No. 1, Art. No. 1, Jan. 2014, doi: 10.3390/s140101073.

I. P. I. Pappas, T. Keller, S. Mangold, M. R. Popovic, V. Dietz, and M. Morari, "A reliable gyroscope-based gait-phase detection sensor embedded in a shoe insole," IEEE Sensors Journal, vol. 4, No. 2, pp. 268-274, Apr. 2004, doi: 10.1109/JSEN.2004.823671.

K. Kong and M. Tomizuka, "A Gait Monitoring System Based on Air Pressure Sensors Embedded in a Shoe," IEEE/ASME Transactions on Mechatronics, vol. 14, No. 3, pp. 358-370, Jun. 2009, doi: 10.1109/TMECH.2008.2008803.

T. Liu, Y. Inoue, and K. Shibata, "Development of a wearable sensor system for quantitative gait analysis," Measurement, vol. 42, No. 7, pp. 978-988, Aug. 2009, doi: 10.1016/j.measurement.2009.02.002.

W. Tao, T. Liu, R. Zheng, and H. Feng, "Gait Analysis Using Wearable Sensors," Sensors (Basel), vol. 12, No. 2, pp. 2255-2283, Feb. 2012, doi: 10.3390/s120202255.

E. S. Sazonov, G. Fulk, J. Hill, Y. Schutz, and R. Browning, "Monitoring of Posture Allocations and Activities by a Shoe-Based Wearable Sensor," IEEE Transactions on Biomedical Engineering, vol. 58, No. 4, pp. 983-990, Apr. 2011, doi: 10.1109/TBME.2010.2046738.

N. Sazonova, R. C. Browning, and E. Sazonov, "Accurate prediction of energy expenditure using a shoe-based activity monitor," Med Sci Sports Exerc, vol. 43, No. 7, pp. 1312-1321, Jul. 2011, doi: 10.1249/MSS.0b013e318206f69d.

N. A. Sazonova, R. Browning, and E. S. Sazonov, "Prediction of Bodyweight and Energy Expenditure Using Point Pressure and Foot Acceleration Measurements," Open Biomed Eng J, vol. 5, pp. 110-115, Dec. 2011, doi: 10.2174/1874120701105010110.

P. H. Veltink, C. Liedtke, E. Droog, and H. van der Kooij, "Ambulatory measurement of ground reaction forces," IEEE Transactions on Neural Systems and Rehabilitation Engineering, vol. 13, No. 3, pp. 423-427, Sep. 2005, doi: 10.1109/TNSRE.2005.847359.

L. Shu, T. Hua, Y. Wang, Q. Li, D. D. Feng, and X. Tao, "In-Shoe Plantar Pressure Measurement and Analysis System Based on Fabric Pressure Sensing Array," IEEE Transactions on Information Technology in Biomedicine, vol. 14, No. 3, pp. 767-775, May 2010, doi: 10.1109/TITB.2009.2038904.

O. Aziz and S. N. Robinovitch, "An Analysis of the Accuracy of Wearable Sensors for Classifying the Causes of Falls in Humans," IEEE Transactions on Neural Systems and Rehabilitation Engineering, vol. 19, No. 6, pp. 670-676, Dec. 2011, doi: 10.1109/TNSRE.2011.2162250.

H. M. Schepers, E. H. F. van Asseldonk, J. H. Buurke, and P. H. Veltink, "Ambulatory Estimation of Center of Mass Displacement During Walking," IEEE Transactions on Biomedical Engineering, vol. 56, No. 4, pp. 1189-1195, Apr. 2009, doi: 10.1109/TBME.2008.2011059.

C. Zhou, J. Downey, D. Stancil, and T. Mukherjee, "A Low-Power Shoe-Embedded Radar for Aiding Pedestrian Inertial Navigation," IEEE Transactions on Microwave Theory and Techniques, vol. 58, No. 10, pp. 2521-2528, Oct. 2010, doi: 10.1109/TMTT.2010.2063810.

E. Foxlin, "Pedestrian tracking with shoe-mounted inertial sensors," IEEE Computer Graphics and Applications, vol. 25, No. 6, pp. 38-46, Nov. 2005, doi: 10.1109/MCG.2005.140.

K. N. Winfree, I. Pretzer-Aboff, D. Hilgart, R. Aggarwal, M. Behari, and S. Agrawal, "An untethered shoe with vibratory feedback for improving gait of Parkinson's Patients: The PDShoe," in 2012 Annual International Conference of the IEEE Engineering in Medicine and Biology Society, Aug. 2012, pp. 1202-1205. doi: 10.1109/EMBC.2012.6346152.

C. B. Redd and S. J. M. Bamberg, "A Wireless Sensory Feedback Device for Real-Time Gait Feedback and Training," IEEE/ASME Transactions on Mechatronics, vol. 17, No. 3, pp. 425-433, Jun. 2012, doi: 10.1109/TMECH.2012.2189014.

C. Mancinelli et al., "A novel sensorized shoe system to classify gait severity in children with cerebral palsy," in 2012 Annual International Conference of the IEEE Engineering in Medicine and Biology Society, Aug. 2012, pp. 5010-5013. doi: 10.1109/EMBC.2012.6347118.

G. D. Fulk and E. Sazonov, "Using Sensors to Measure Activity in People with Stroke," Topics in Stroke Rehabilitation, vol. 18, No. 6, pp. 746-757, Nov. 2011, doi: 10.1310/tsr1806-746.

G. D. Fulk, S. R. Edgar, R. Bierwirth, P. Hart, P. Lopez-Meyer, and E. Sazonov, "Identifying Activity Levels and Steps in People with Stroke using a Novel Shoe-Based Sensor," J Neurol Phys Ther, vol. 36, No. 2, pp. 100-107, Jun. 2012, doi: 10.1097/NPT.0b013e318256370c.

"DigiBarn Weird Stuff: Puma RS Computer Tennis Shoes (pedometer, 1980s)." https://www.digibarn.com/collections/weirdstuff/computer-tennis-shoes/ (accessed Nov. 10, 2021).

V. L. Houston, G. Luo, C. P. Mason, M. Mussman, M. Garbarini, and A. C. Beattie, "Changes in Male Foot Shape and Size with Weightbearing," Journal of the American Podiatric Medical Association, vol. 96, No. 4, pp. 330-343, Jul. 2006, doi: 10.7547/0960330.

* cited by examiner

SENSORIZED SHOELACE-TENSIONING SYSTEM AND METHOD

CROSS-REFERENCE TO RELATED APPLICATION

This application claims priority to and benefit of U.S. provisional patent application Ser. No. 63/148,756 filed Feb. 12, 2021, which is fully incorporated by reference and made a part hereof.

GOVERNMENT SUPPORT

This invention was made with government support under grant number 1734501 awarded by the National Science Foundation (NSF). The government has certain rights in the invention.

TECHNICAL FIELD

The present disclosure relates to devices, systems and methods related measuring movement of a person. In particular, to devices, systems and methods are described for measuring movement associated with a person's foot.

BACKGROUND

Disclosed are devices and articles of manufacturer, and methods of using the same that generally relate to sensors and sensor components, as well as the applications of the sensors/sensor components such as activity monitoring.

The existing products serving similar purposes are the wearable inertia measurement units (IMUs) as standalone sensors or embedded sensors within smart wearable devices (such as smart watches and wrist bands). Standalone IMUs usually need to mounted to human body with straps, which is inconvenient and unreliable in daily-use. Smart wearable devices are usually worn on wrists, and thus are unable to provide information directly related to the wearers' full-body/lower-limb motion. As such, the estimation of the wearers' activity and energy expenditure is inaccurate and unreliable. Additionally, there is a shoe insole-based sensor kit as well as a sensor-embedded smart shoe product manufactured by Nike, but the durability of these products are not satisfactory.

Foot-worn IMUs and pressure sensors are used to determine weight, posture allocation, physical activity classification, and energy expenditure calculations, among other parameters related to motion of the foot (gait) and/or person of the wearer. Such an IMU and use is described in U.S. Pre-Grant Publication 2011/0054359 A1 to Sazonov et al., published Mar. 3, 2011, which is fully incorporated by reference and made a part hereof.

However, these prior IMUs have not been able to determine ankle movement and require pressure sensors in the insole to determine foot loading.

Therefore, what are needed are systems and methods that overcome challenges in the art, some of which are described above.

SUMMARY

Compared with existing technologies described above, the device, systems and methods described in this disclosure provides a smart sensor that can be easily and reliable mounted to the wearer's foot with at least a portion in the form of a shoelace attachment. The use of this sensor in people's daily life is almost effortless. Further, the rich information provided by this sensor enables it to provide far more accurate information on the wearer's activity mode, energy expenditure, and gait quality, compared with the existing wrist-mounted smart devices. Furthermore, this new sensor can be used in conjunction with the wrist-mounted smart devices to form a more comprehensive understanding of the user's full-body movement, providing the potential of integrating into the existing health monitoring eco system and creating a synergy far exceeding the efficacy of each individual technology.

Other systems, methods, features and/or advantages will become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

The present disclosure relates to techniques for gripping and positioning of sensors on feet as well as using these sensors and in receiving gait and/or mobility data from one or more sensors and controlling the use and redistribution of that data so it is used in an intended manner.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Figure 1A:
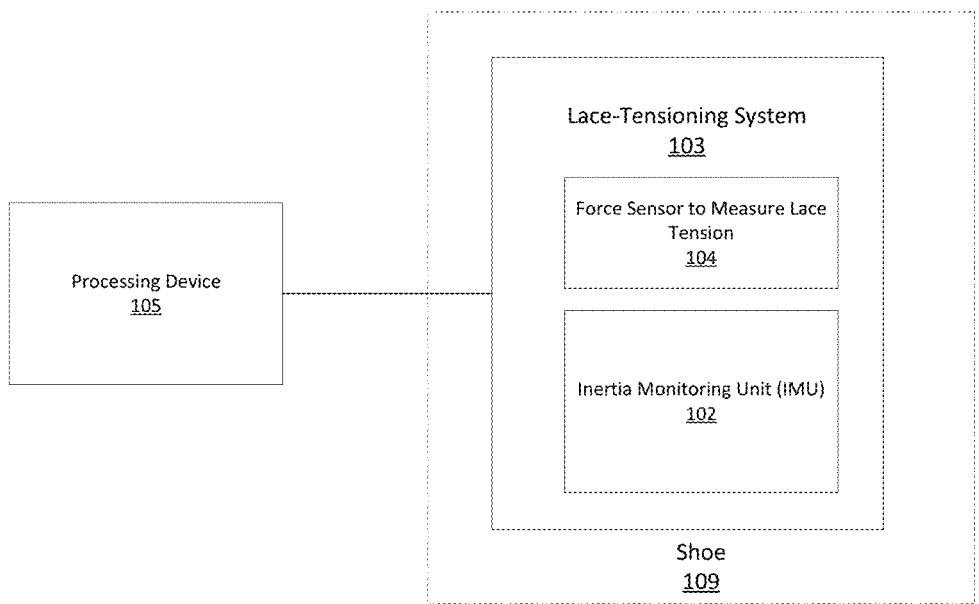
FIG. 1A illustrates an exemplary block diagram of a system for measuring motion of a shoe and lace tension of the shoe.

FIG. 1A is a block diagram of an exemplary system 100 for measuring motion of a shoe and lace tension of the shoe. The system 100 comprises a shoe 109. Attached to the laces of the shoe 109 is a lace-tensioning system 103. As will be further described below, the lace-tensioning system 103 may be attached to any normal shoe 109 having laces or other means for tightening the shoe about the foot (e.g. Velcro™ (i.e., loop and hook) straps, elastic, etc.). Hereinafter, any means of for tightening the shoe about the foot shall be referred to as "laces", "shoelaces" or "shoe strings." Once installed, the lace-tensioning system 103 can be used to tighten and loosen the shoe strings so that they do not have to be re-tied each time the shoe 109 is worn, or untied when the shoe 109 is being removed. As shown in FIG. 1A, the lace-tensioning system 103 further comprises an inertia monitoring unit (IMU) 102, described in more detail in reference to FIG. 1B. The lace-tensioning system 103 includes a force sensor 104 configured to detect changes in the amount of force (including tension) exerted on the shoelaces during stationary postures and motion (including walking) of the wearer's foot. One non-limiting example of a lace-tensioning system force sensor is a load cell.

Figure 1B:
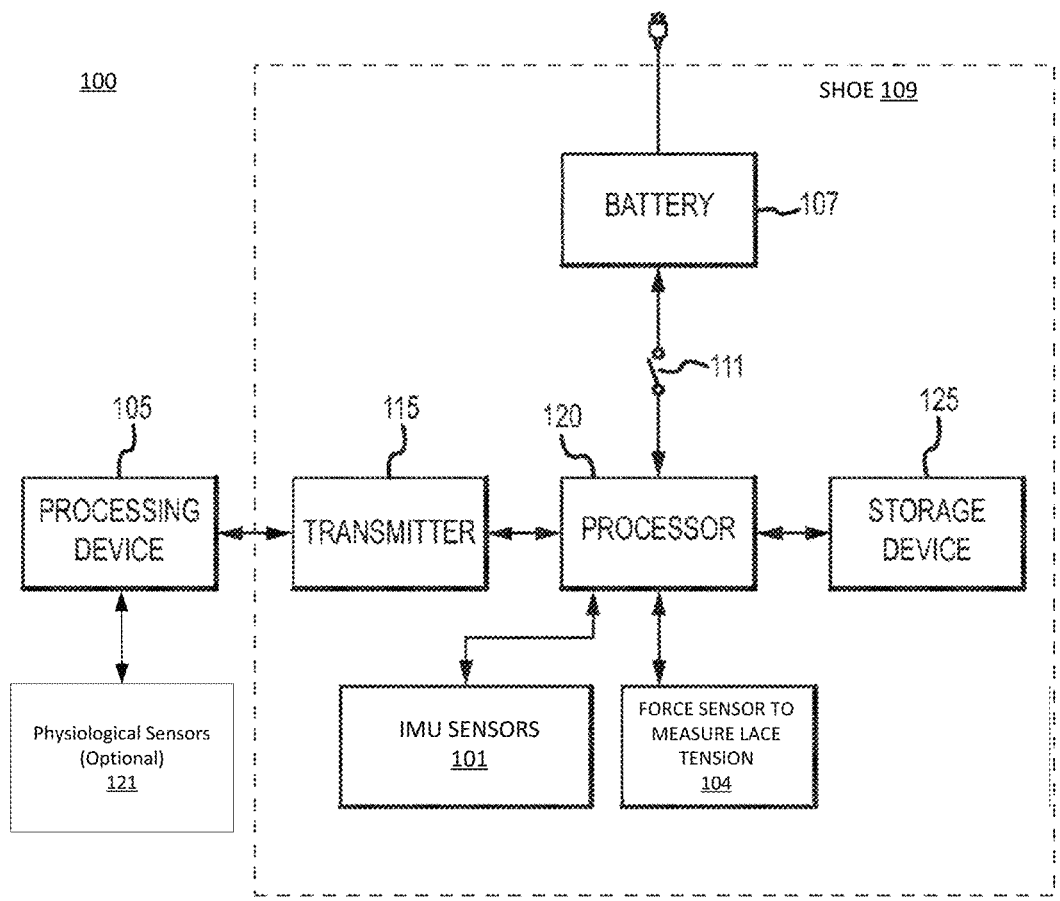
FIG. 1B illustrates a schematic diagram of the monitoring system shown in FIG. 1A.
Figures 1C, 1D:
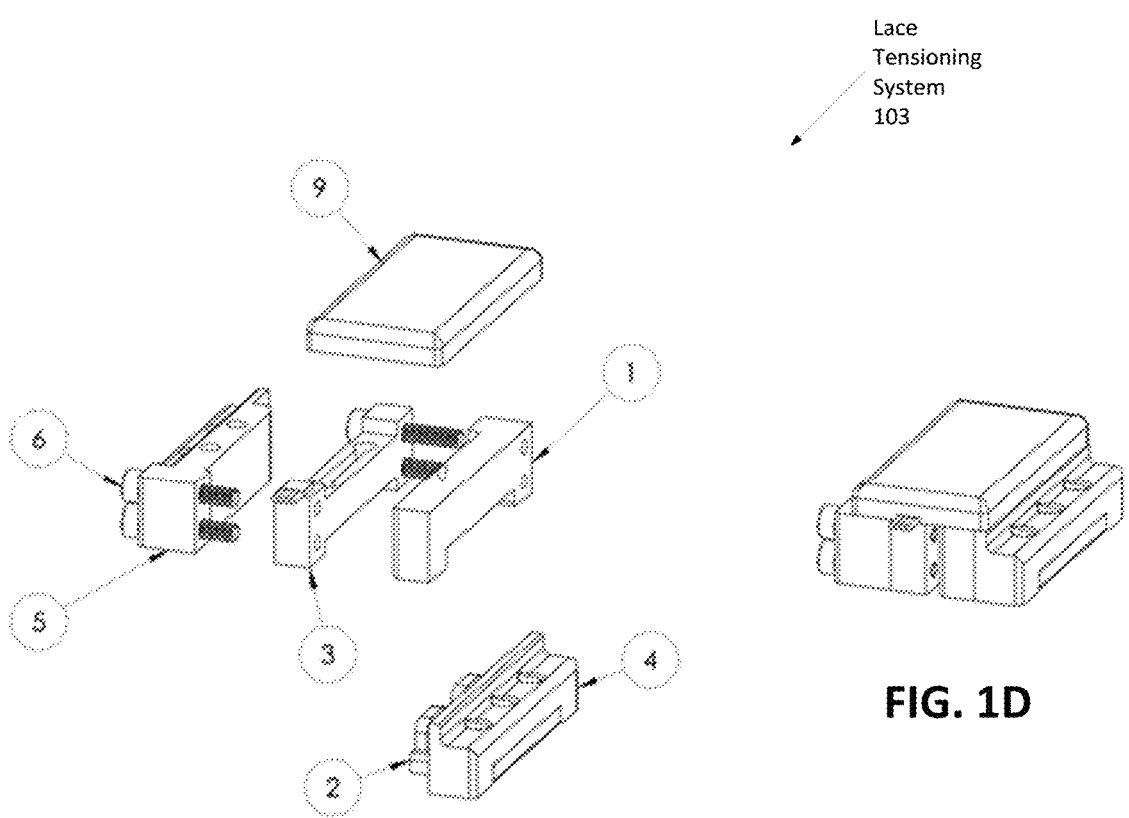
FIGS. 1C and 1D illustrates an example of a lace-tensioning system.

One non-limiting example of a lace-tensioning system 103 is described in greater detail herein in reference to FIGS. 1C and 1D, though other embodiments of a lace-tensioning system are contemplated within the scope of this disclosure. The lace-tensioning system 103 and its IMU 102, alone or in combination, may be configured to detect changes in force to identify and differentiate between various parts of the user's gait cycle, including, but not limited to, heel strike, stance phase and toe-off, as well as account for differences in the loading of anterior and posterior areas of the user's foot. The system may also be used to differentiate static postures such as sitting and standing, and weight-bearing and non-weight bearing activities such as riding a bike or walking.

FIG. 1B illustrates a schematic diagram of the monitoring system 100 shown in FIG. 1A. As shown in FIG. 1B, each monitoring system 100 may include a shoe 109, a lace-tensioning system 103 comprising a force sensor to measure lace tension 104 and an IMU 102 comprising IMU sensors 101. As shown in FIG. 1B, the system 100 further comprises a battery 107, a power switch 111, and a transmitter 115 configured to transmit data to a processing device 105. In some instances, IMU 102 may comprise a special type of micro electro-mechanical system (MEMS) providing acceleration and angular velocity measurement in the three-dimensional space.

The monitoring system 100 further includes a processor 120 that is connected to IMU sensors 101, and the force sensor to measure lace tensioning 104. Generally, IMU sensors 101 include one or more sensors such as of an accelerometer, a gyroscope, a magnetometer, and a barometer (each collectively shown as element 101 in FIG. 1B). The IMU sensors 101 may be configured to measure the physical acceleration experienced by the user's feet as well as orientation of the foot in respect to the Earth coordinates, foot trajectory, elevation and change in elevation. In some embodiments, one of the IMU sensors 101 may be an accelerometer and the accelerometer may be a one-dimensional accelerometer, a two-dimensional accelerometer, or a three-dimensional accelerometer. One example of a two-dimensional accelerometer that may be used in conjunction with the disclosed embodiments is a two-dimensional MEMS accelerometer, which is configured to measure sagittal plane accelerations of the user's feet. An example of a three-dimensional accelerometer that may be used in conjunction with the disclosed embodiments is an LIS3L02AS4 MEMS accelerometer, which is configured to measure accelerations of the user's shoes 109 in three or more orthogonal directions. It should be appreciated that other embodiments may use one or more accelerometers, gyroscopes, magnetometers, and barometers mounted to other portions of the user's shoes or body, and that the sensors 101 may sense in other desired planes, such as the coronal plane.

The processor 120 may also be connected to any (optional) physiological sensors 121 through the processing device 105. The processor 120 may be configured to sample and process the data collected by the IMU sensors 101 and/or the force sensor to measure lace tensioning 104. Additionally, the processor 120 may be connected to a storage device 125, and may be configured to store sampled data in the storage device 125 for later transmission.

Referring to FIG. 1B, the power switch 111 may be configured to activate and deactivate the monitoring system 100 through the processor 120, which may be coupled to the IMU sensors 101, the force sensors to measure lace tensioning, and the transmitter 115. Power may be supplied by the battery 107, which may be a rechargeable or a non-rechargeable battery, or alternatively, from any AC or DC power source connected to the monitoring system 100, an energy harvester, such as a solar cell, a piezoelectric harvester, and so on and so forth. In an alternative embodiment, the battery 107 may be directly coupled to each or some of the IMU sensors 101, the force sensor for measuring lace-tensioning 104, the transmitter 115, and the (optional) physiological sensor 121 so as to provide power to these components individually, rather than through the processor 120. In some instances, the battery 107 and the power switch 111 may be part of the lace-tensioning system 103, while in other instances one or more of the battery 107 and the power switch 111 may be separate from the lace-tensioning system 103.

In one embodiment, the monitoring system 100 may also include an activation mechanism configured to allow the user to activate and deactivate the monitoring system 100. The activation mechanism may be a mechanism provided on the user's shoe 109, such as a switch, button, lever, motion sensor, pressure sensor (resistive or capacitive), etc. or may be a device that is remotely connected to the monitoring system 100, such as a remote control, a remote motion sensor, the processing device 105, etc.

In some instances, the lace-tensioning system 103 may be configured to activate and deactivate the monitoring system 100. For example, the lace-tensioning system 103 may be configured to activate the monitoring system 100 when the user is wearing the shoes 109, i.e., when force (including tension) is applied to the lace-tensioning system 103, and deactivate the monitoring system 100 when the user is not wearing the shoes 109, i.e., when no pressure (including tension) is applied to the lace-tensioning system 103. In other embodiments, the lace-tensioning system 103 may further be configured to place the monitoring system 100 into a low-power, or "sleep" state when the lace-tensioning system 103 determines that the user is not wearing one or both shoes 109. The "sleep" state may serve to prolong the battery life of the monitoring system 100. In some instances, the lace-tensioning system 103 comprises two parts (see Assembly A and Assembly B of FIGS. 1C and 1D, herein referred to as the "lace-tensioning assemblies") that are configured to lock together and unlock, which can serve as a "switch" when the two pieces are connected together to turn on the monitoring system 100 and turn it off when the two pieces are disconnected.

The transmitter 115 may be connected to the processor 120 of the monitoring system 100, and may be configured to transmit sampled data collected by the IMU sensors 101 and/or the force sensor to measure lace-tensioning 104 to a processing device 105 that is configured to process the received data. The data transmission may be through either a wired or a wireless transmission medium. In one embodiment, the transmitter 115 may be a wireless transmitter, and may use a wireless protocol for communicating with the processing device. For example, the transmitter 115 may use Bluetooth, ZigBee, Wi-Fi (IEEE 802.11n), ANT protocols and systems, and the like. In one embodiment, the wireless protocol may be a low-power consumption protocol that preserves the battery life of the battery 107. In some instances, the transmitter 115 may comprise the interface 1327 shown and described with reference to FIG. 3. Generally, the portion of the system 100 on the shoe 109 is in communication with the processing device 105 using the transmitter 115. This processing device 105 may be, for example, a smart phone or some other form of wearable smart electronics such as a fitness monitor, fitness watch, and the like. The processing device 105 may be a dedicated electronic device or a ubiquitous electronic device that is configured to perform other functions. Some examples of electronic devices that may be used in conjunction with the disclosed embodiments include, but are not limited to, a personal computer, such as a laptop, tablet PC or a handheld PC, a PDA, a mobile telephone, a media player, such as an MP3 player, a television receiver, and the like. The processing device 105 may run monitoring software configured to process the collected data and provide feedback to the user regarding the collected data. For example, the monitoring software may use the collected data to calculate the weight and energy expended by the user; identify human activity modes and estimating energy expenditure (how many calories are burned?); monitor gait quality in daily life, detecting unexpected gait events (e.g., tripping, slipping, and falling), and estimating the risk of fall for frail older adults and individuals with neuromuscular pathologies (stroke, spinal cord injury, Parkinson's disease, etc.); quantify the rehabilitation outcomes in real-world daily-living environments (i.e., outside clinics and labs); support the adaptive control of wearable assistive devices (lower-limb prostheses and exoskeletons) through the real-time measurement of healthy-side leg movements; and quantify the performance of athletes in sports and provide this information to the user (or others) as feedback. The portion of the system 100 on the shoe 109 will generally communicate wirelessly with the processing device 105 as described above, though wired communication may also be used. The processing device 105 may be in communication with a network and/or other processing devices such as, for example, the internet, through WAN/LAN/Wi-Fi, cellular data communications, and the like. In some instances, the processing device 105 may interact with a cloud computing architecture.

As noted herein, some embodiments of the monitoring system 100 may further include one or more physiological sensors 121 that are also connected to the processing device 105. For example, the physiological sensor 121 may be a bioelectric sensor that is configured to detect electric currents that flow in a user's nerves and muscles, such as the user's heart. In other embodiments, the physiological sensor 121 may be a heart monitor, a piezoelectric pulse monitor, a reflectance optical oximeter configured to detect oxygenation and/or pulse, a respiration sensor, a galvanic skin response sensor, a skin temperature sensor, and so on and so forth. The physiological sensor 121 may be connected to any part of the user's body through either a wired or a wireless connection. For example, the physiological sensor 121 may be positioned directly on the user's skin, over the user's clothing, or in one or both of the user's shoes as an insertable insole, in the user's socks, etc.

FIGS. 1C and 1D are illustrations of an embodiment of a lace-tensioning system 103. This embodiment is comprised of female coupler (1), male coupler (2), force sensor (e.g., load cell) (3), the lace-tensioner assemblies including lace tensioner B (4) and lace tensioner A (5), screws (6), and electronics enclosure (7) that contains at least an IMU. Herein, the female coupler (1), male coupler (2), load cell (3), the lace-tensioner assemblies including lace tensioner B (4) and lace tensioner A (5), and screws (6), if needed, may be referred to collectively as the lace-tensioning device. In some instances, the force sensor (3) comprises a small force sensor (load cell) configured to measure the combined force applied by the shoelace on each side of the lace tensioner assemblies. In other instances, the force sensor comprises distributed force sensors to measure the shoelace forces applied to individual routing holes; and/or flat force sensors on the bottom surface of the lace tensioning system 103 to measure the (overall or distributed) force(s) applied by the system 103 to the top surface of the shoe. In some instances, a combination of force sensors may be used by the system 103.

Figure 1E:
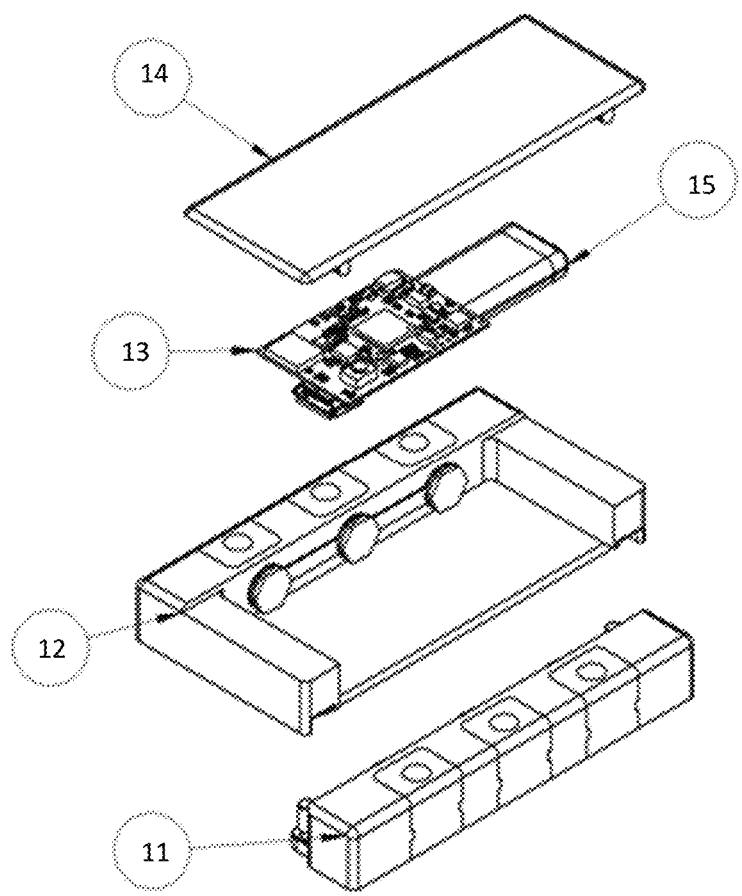
FIGS. 1E, 1F and 1G illustrate alternative examples of a lace-tensioning system.
Figure 1F:
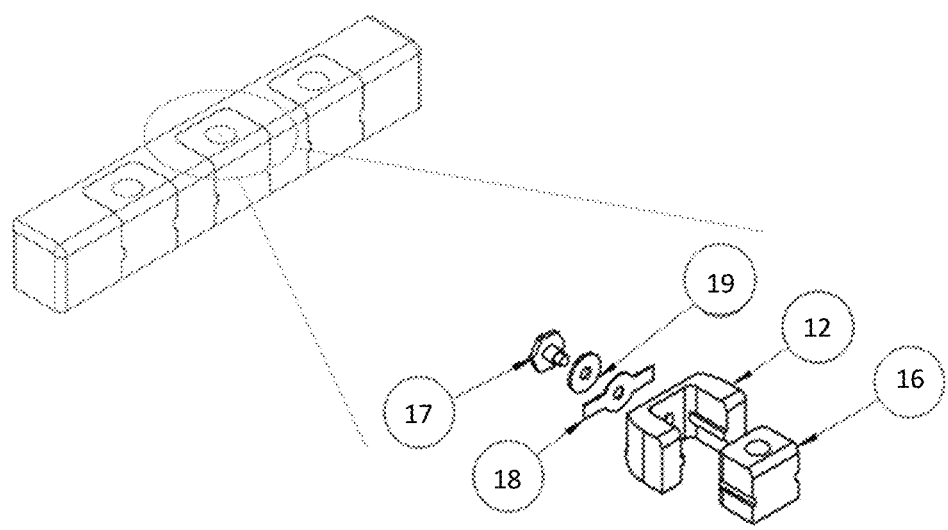
Figure 1G:
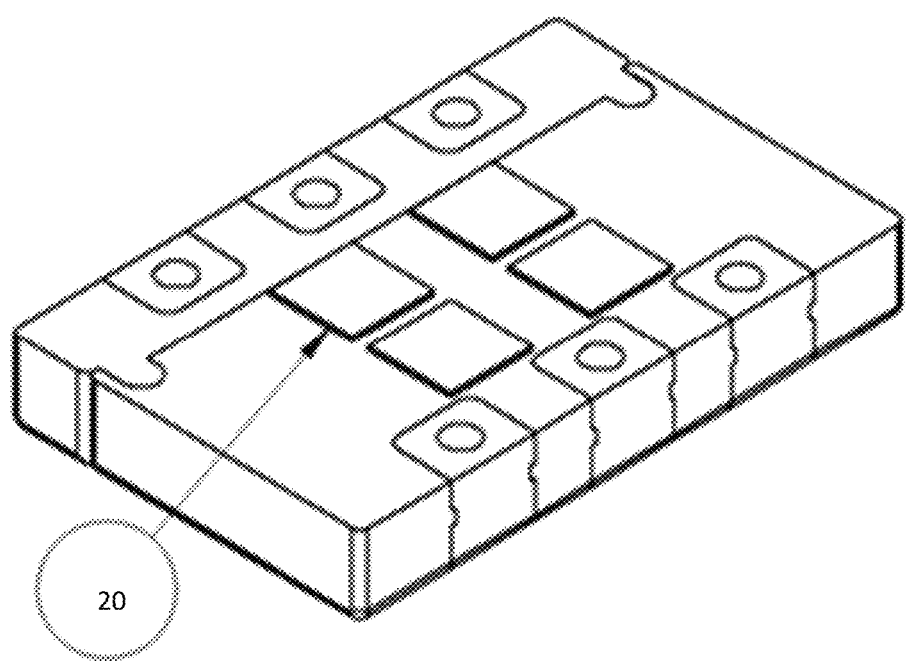

FIG. 1E illustrates an embodiment where distributed force sensors are used to measure the shoelace forces applied to individual routing holes comprised of lace tensioner B (11); Lace Tensioner A base (12) (for the installation of the other components 13, 14, and 15); circuit board/IMU (13); lace tensioner A cover; and battery (15). Referring now to FIG. 1F, each shoelace routing hole is embedded in a separate sliding block (16) that may move outwards when shoelace tension is applied. Specifically, in one non-limiting example, a flanged pin (17), after going through a hole in the lace tensioner A (11) or B (12), is rigidly connected to a sliding block (16). When the shoelace force pulls the sliding block outwards, the flange of the flanged pin (17) applies a compression force to a force sensing pad (18) through a compressible washer (19). The force sensing pad (18) generates an electronic signal to measure the applied compression force. With every routing hole instrumented with this method, the distributed force sensors measures all the individual forces applied by the shoelace, which provides rich information about how the ankle moves, how the foot shapes changes, and how much load the foot applies to the ground. For surface-mounted force-sensing pads, as shown in FIG. 1G, the bottom (shoe-facing) side of the system 103 can be attached with one or more force-sensing pads (20), which measure the surface contact forces between the bottom of the system 103 and the top surface of the shoe. The measured force signals may also change with the ankle movement, foot shape change, and foot plantar force, and thus provide additional information about the human movement and the human's interaction with the environment (ground).

The shown embodiment comprises two lace-tensioner assemblies (Assembly A and Assembly B) in the detached (i.e., unlocked) state, as shown in FIG. 1C. Lace-tensioner assembly A is comprised of lace tensioner A (5), load cell (3), and female coupler (1), connected with screws (6). Lace tensioner assembly A (5) and lace tensioner assembly B (4) have a number of holes to route the shoelace. In other instances, bores, slots, hooks, rings and the like may be provided that allow the user to tie the lace tensioners (4, 5) to his or her shoelaces. Other attachment mechanisms are also possible, as are well known in the art.

In addition, in some instances an electronics enclosure (9), attached to the lace tensioner A (5) or female coupler (1), may also comprise part of Assembly A or Assembly B. In some instances, the electronics enclosure (9) houses one or more of an inertia measurement unit (IMU) as described herein, comprising a load cell signal conditioning circuit, a microprocessor, a battery, and the other electronic components and circuit boards for sensor interfacing, data processing and storage, and wireless/wired communication. In other instances, the lace-tensioning system 103 may connect to (wired or wirelessly) and communicate with a separately attached IMU 102, as shown and described herein.

Lace-tensioner assembly B of the lace-tensioning system 103 is comprised of lace tensioner B (4) attached with a male coupler (2). Similar to the lace tensioner A (5), the lace tensioner B (4) also has a number of holes to route the shoelace, or other attachment mechanisms as described herein.

To use the lace-tensioning system 103, each assembly is attached to one side of the shoe, with the shoelace routed through the holes in the lace tensioners A (5) and B (4) or otherwise attached to lace tensioners A (5) and B (4). Subsequently, the two assemblies (Assembly A and Assembly B) are securely attached to each other by inserting the teeth of the male coupler 2 into the slots in the female coupler (1). The lace-tensioning system 103 in the locked state is shown in FIG. 1D. For the reliability of attachment, both the male coupler 2 and female coupler 1 may have a magnet embedded on the mating surface, such that the pulling force between the magnets ensures the assemblies to stay together in the locked state. To unlock, the Assembly A should be lifted upwards such that the teeth of the male coupler (2) slide out of the slots in the female coupler (1). As such, the assemblies can be attached and detached with minimum efforts from the user. Tension in the shoelaces is measured by the load cell 3, which is the force sensor for the lace-tensioning system 103. Other types of force sensors may also be used, such as piezoelectric load cells, piezoresistive sensors, optical sensors and others.

Figure 2A:
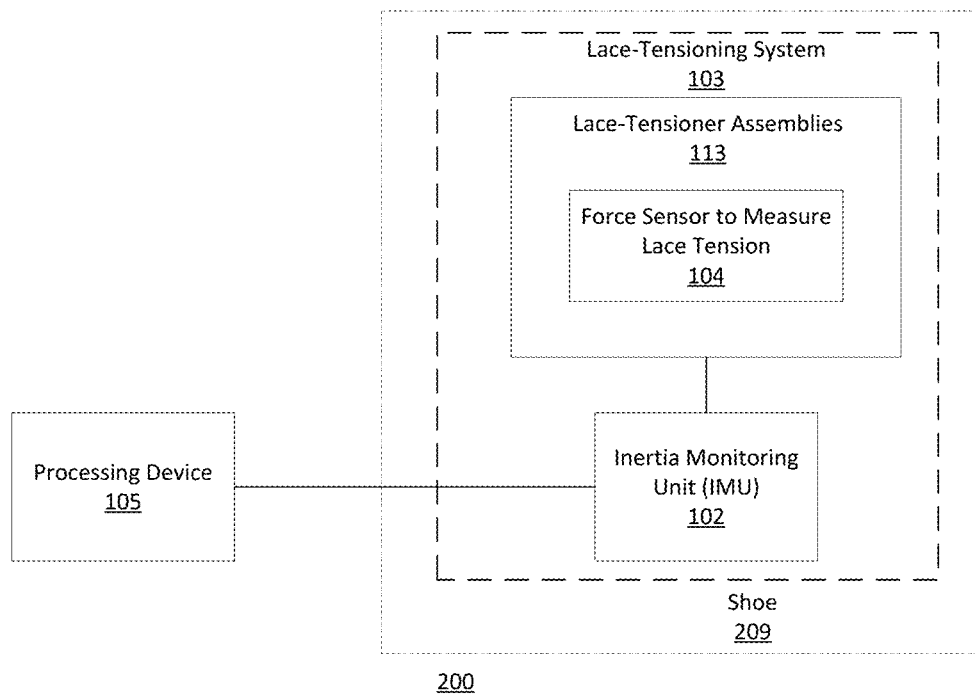
FIG. 2A is a block diagram of an alternate embodiment of an exemplary system for measuring motion of a shoe and lace tension of the shoe.

FIG. 2A is a block diagram of an alternate embodiment of an exemplary system 200 for motion of a shoe and lace tension of the shoe. In this embodiment, lace tensioner assemblies 113, including the force sensor to measure lace tension 104, is attached to the laces of the shoe 209, but the IMU 102 and/or other electronics of the system 100 (including one or more of battery 107, switch 111, processor 120, transmitter 115 and storage device 125) are connected to another location of the shoe 209 and/or foot. The force sensor to measure lace tension 104 may be any device capable of measuring force (tension) including a load cell, piezoelectric load cells, piezoresistive sensors, optical sensors and the like. The IMU 102 and/or other electronics of the system 100 may be attached to any location on the shoe 209. For example, the IMU 102 and/or other electronics of the system 100 may be attached to the back of the shoe 209, a side of the shoe 209, attached to the tongue of the shoe 209, or attached to the shoelaces of the shoe 209 along with the lace-tensioning system 103. As described above, in some instances, while the IMU 102, other electronics of the system 100, and the lace-tensioning system 103 are a single device and/or share common housing, yet in other instances, they are separate device components and communicate with each other through wires or wirelessly.

Figure 2B:
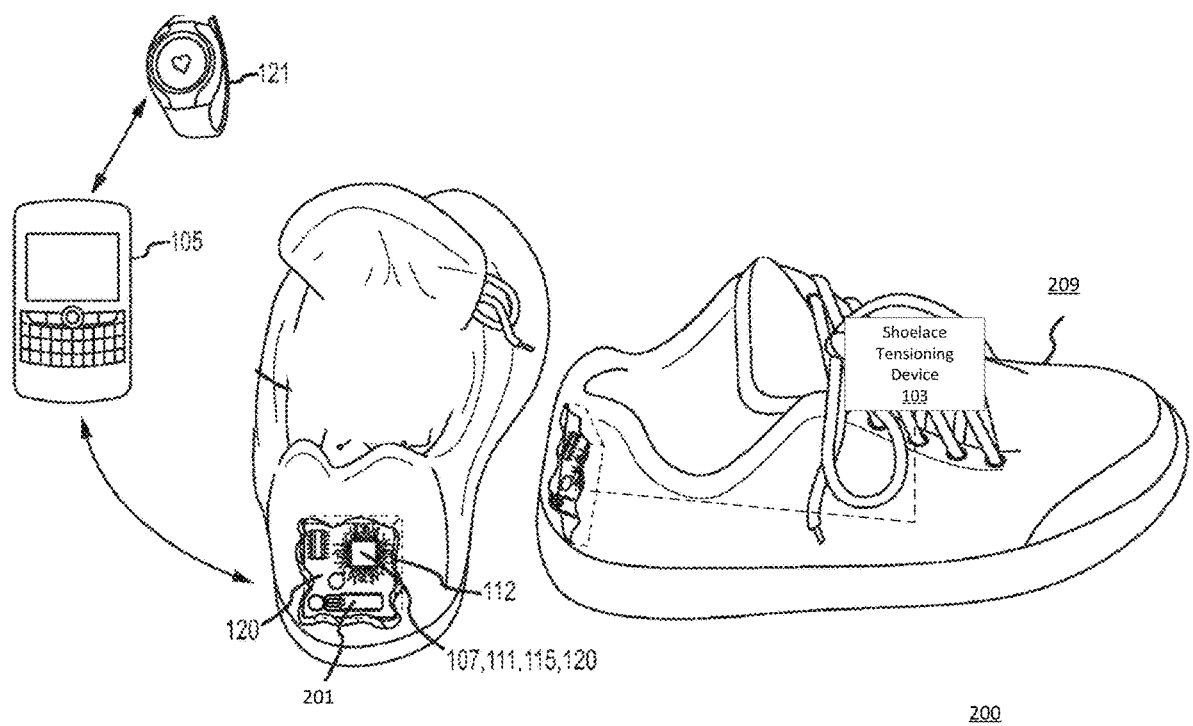
FIGS. 2B and 2C illustrate two alternate embodiments of footwear-based monitoring systems for measuring motion of a shoe and lace tension of the shoe.
Figure 2C:
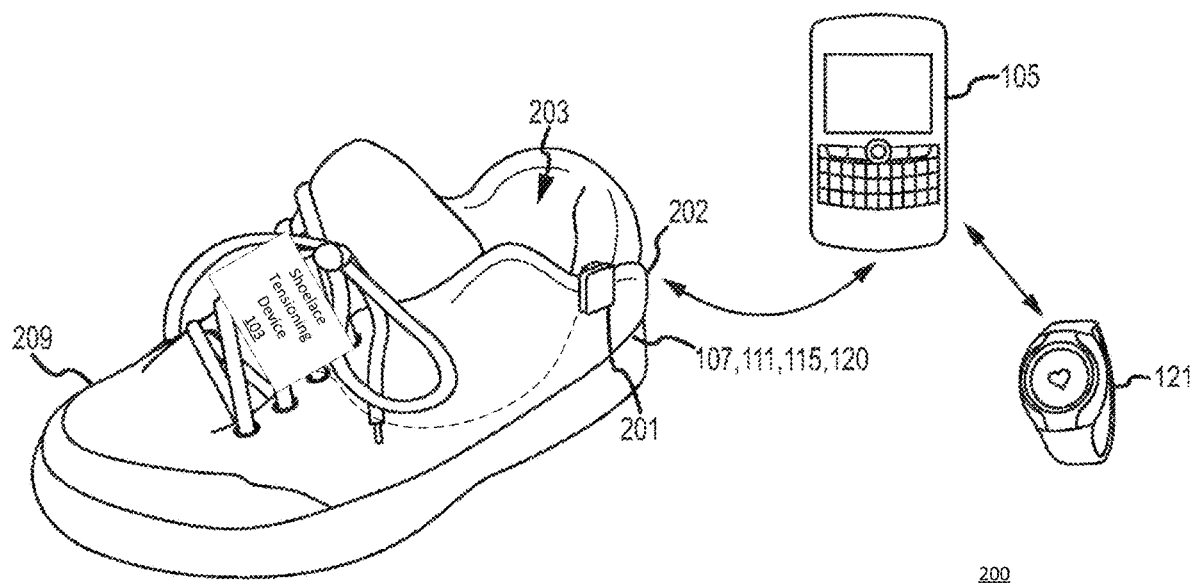

FIGS. 2B and 2C illustrate two examples alternate embodiments of footwear-based monitoring systems 200, as described herein. Generally, each of these monitoring systems 200 also include one or more IMU sensors 101 such as of an accelerometer, a gyroscope, a magnetometer, and a barometer (each also collectively shown as element 101 in FIGS. 2B and 2C), and a lace-tensioning system 103 comprising, for example, a force sensor for measuring shoelace tension 104. IMU sensors 101 and lace-tensioning system 103 are communicatively connected to the processing device 105, which is configured to process data received from the lace-tensioning system 103 including the one or more IMU sensors 101.

In one embodiment, as shown in FIG. 2B, the IMU sensors 101, and other electronics including battery 107, power switch 111, transmitter 115, processor 120, and circuit board 112 may be embedded in the user's shoe 209, for example, in the heel or back portion and the lace-tensioning assemblies are attached to the shoe strings. In another embodiment, as shown in FIG. 2C, the IMU 201 and other electronics including battery 107, power switch 111, transmitter 115, processor 120 may be provided in a clip-on device 202 that is releasably attachable to the user's shoe 209 and the lace-tensioning assemblies are attached to the shoe strings. In other embodiments, as described herein, other sensors 121 may be otherwise worn by the user. In other instances, some other releasable attachment mechanism allows a user to conveniently attach and remove the IMU 201 and other electronics from the shoe 209 or sock. For example, other embodiments of the IMU 201 may include one or more bores, slots, hooks, rings and the like that allow the user to attach the IMU 201 and other electronics to his or her shoelaces. In another embodiment, the attachment mechanism may be a band that is adjustable in size so as to allow the user to attach the band around the user's ankle, leg, arm, or some other body part. Other attachment mechanisms are also possible, as are well known in the art.

The sensors, battery, power switch, and/or transmitter may be more or less distributed in other embodiments. For example, the sensors and the transmitter may be integrated into the shoe, while the battery and the power switch maybe provided on a separate device.

The IMU 102, 201, other electronics, and/or the lace-tensioning assemblies of the lace-tensioning system 103 may be connected to or integrated into or one or both of the user's shoes 109, 209. Accordingly, the monitoring system 100, 200 may be configured to collect motion information such as acceleration, angular velocity, orientation in respect to gravity, foot trajectory and foot elevation and lace tension information from one of the user's shoes 109, 209, or both of the user's shoes. It should be noted that in other embodiments, the IMU 102, 201 and other electronics may be connected to or integrated into the user's clothing, Such as the user's socks, or may be independently coupled to the user, such as through an arm band, leg band, or some other attachment mechanism.

The data obtained from the IMU 102, 201 of the lace-tensioning system 103 may be used to classify the type of motion-based activity that the user is performing (e.g., walking vs. running), quantify the amount of body motion in static postures (e.g., shifts in body weight while standing), and distinguish between movement performed along a level surface from movement performed along an inclined (i.e., uphill or downhill) surface, such as a gradually inclined surface, stairs, etc. The gait cycle identification and loading profiles may also be used to detect asymmetries in the gait pattern indicating fatigue or potential development of injury. Additionally, data regarding key temporal and spatial gait parameters, including, but not limited to, cadence, stride length, and stance time, may be extracted from the data and used to characterize the user's movement-based activities and provide feedback to the user. For example, the feedback may include the number of steps taken by the user, distance walked, cadence, etc.). Data obtained from the IMU 102, 201 of the lace-tensioning system 103 may also be used to measure the overall motion of the wearer's leg and foot during the leg's swing. Further, it may also measure the motion of the foot when it is pushing off the ground to obtain the forward momentum in walking or running, and thus provide an effective method to quantify the quality of the gait, the strength of the leg muscles, the overall health of the wearer, a person's postures, physical activity and transitions between postures and activities, and measurements of quantifiable and qualitative characteristics of these postures, activities, and transitions. determining the overall health of the person may include identifying human activity mode, postures, and transitions between different activities/postures and/or estimating energy expenditure and/or quantifying rehabilitation outcomes of the person in real-world daily-living environments. Identifying human activity modes, postures, and transitions between different activities/postures may comprise identifying one or more of identifiable activities and postures including but not limited to sitting, standing, sit to stand, stand to sit, walking, running, stair ascent, stair descent, and cycling.

Figure 3:
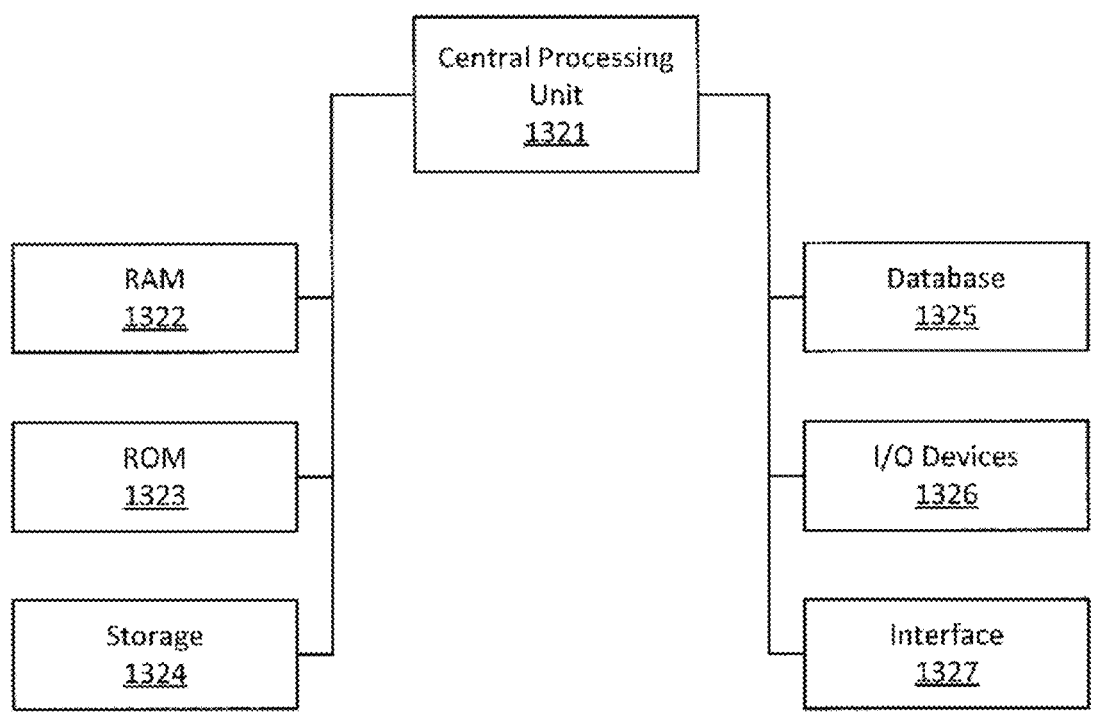
FIG. 3 illustrates an exemplary computer for use with the disclosed embodiments.

FIG. 3 illustrates an exemplary computer. Processing device 105, processor 120, storage device 125, transmitter 115. and intermediate devices, cloud computing architecture and associated servers to which the processing device 105 may communicate, as well as other system components, can include all or some of the components shown in FIG. 3 and described below.

The computers may include one or more hardware components such as, for example, a central processing unit (CPU) 1321, a random-access memory (RAM) module 1322, a read-only memory (ROM) module 1323, a storage 1324, a database 1325, one or more input/output (I/O) devices 1326, and an interface 1327. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 1324 may include a software partition associated with one or more other hardware components. It is understood that the components listed above are exemplary only and not intended to be limiting.

CPU 1321 may include one or more processors, each configured to execute instructions and process data to perform one or more functions associated with a computer for monitoring gait and/or mobility levels. CPU 1321 may be communicatively coupled to RAM 1322, ROM 1323, storage 1324, database 1325, I/O devices 1326, and interface 1327. CPU 1321 may be configured to execute sequences of computer program instructions to perform various processes. The computer program instructions may be loaded into RAM 1322 for execution by CPU 1321.

RAM 1322 and ROM 1323 may each include one or more devices for storing information associated with operation of CPU 1321. For example, ROM 1323 may include a memory device configured to access and store information associated with controller 1220, including information for identifying, initializing, and monitoring the operation of one or more components and subsystems. RAM 1322 may include a memory device for storing data associated with one or more operations of CPU 1321. For example, ROM 1323 may load instructions into RAM 1322 for execution by CPU 1321.

Storage 1324 may include any type of mass storage device configured to store information that CPU 1321 may need to perform processes consistent with the disclosed embodiments. For example, storage 1324 may include one or more magnetic and/or optical disk devices, such as hard drives, CD-ROMs, DVD-ROMs, or any other type of mass media device.

Database 1325 may include one or more software and/or hardware components that cooperate to store, organize, sort, filter, and/or arrange data used by CPU 1321. For example, database 1325 may data relating to monitoring gait and/or mobility levels, associated metadata, and health information. It is contemplated that database 1325 may store additional and/or different information than that listed above.

I/O devices 1326 may include one or more components configured to communicate information with a user associated with the device shown in FIG. 3. For example, I/O devices 1326 may include a console with an integrated keyboard and mouse to allow a user to maintain a database of images, update associations, and access digital content. I/O devices 1326 may also include a display including a graphical user interface (GUI) for outputting information on a monitor. I/O devices 1326 may also include peripheral devices such as, for example, a printer for printing information associated with controller 1220, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1327 may include one or more components configured to transmit and receive data via a communication network, such as the Internet, a local area network, a workstation peer-to-peer network, a direct link network, a wireless network, or any other suitable communication platform. For example, interface 1327 may include one or more modulators, demodulators, multiplexers, demultiplexers, network communication devices, wireless devices, antennas, modems, and any other type of device configured to enable data communication via a communication network.

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object-oriented programming language such as Java, Smalltalk, C++, or the like, and conventional procedural programming languages, such as the "C" programming language or similar programming languages. The program code may execute entirely on the computing unit.

Figure 4A:
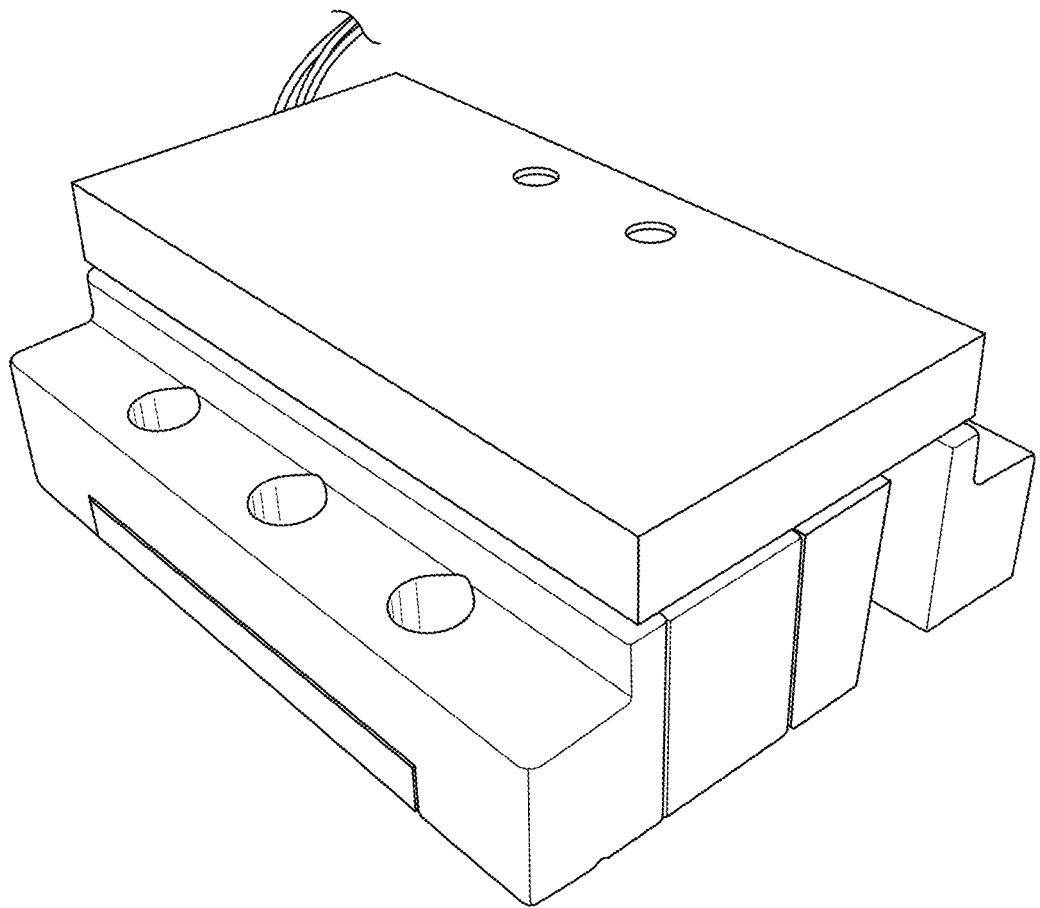
FIGS. 4A-4D illustrate photographs of disclosed embodiments of an exemplary lace-tensioning system.
Figure 4B:
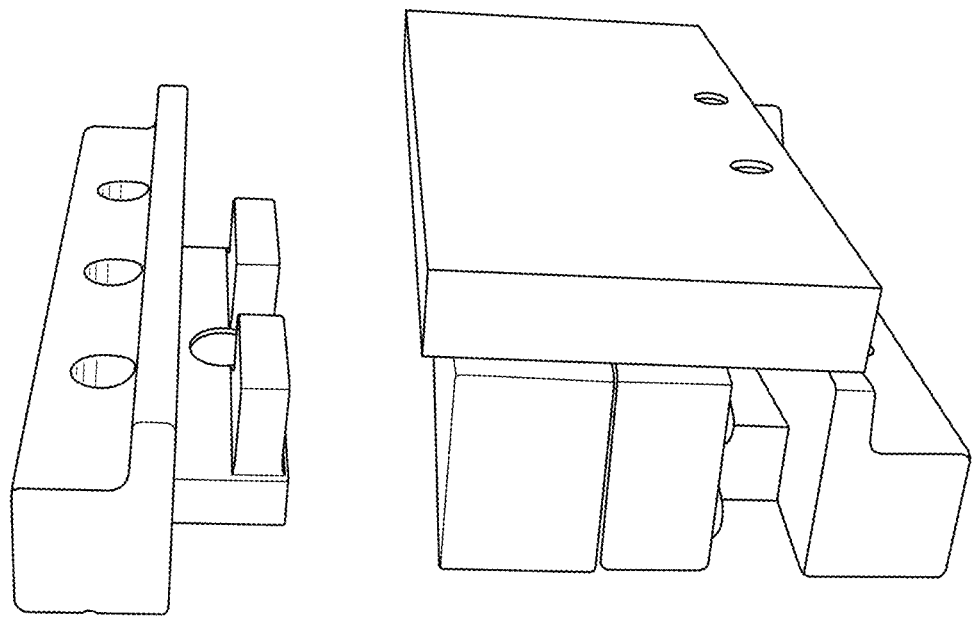
Figure 4C:
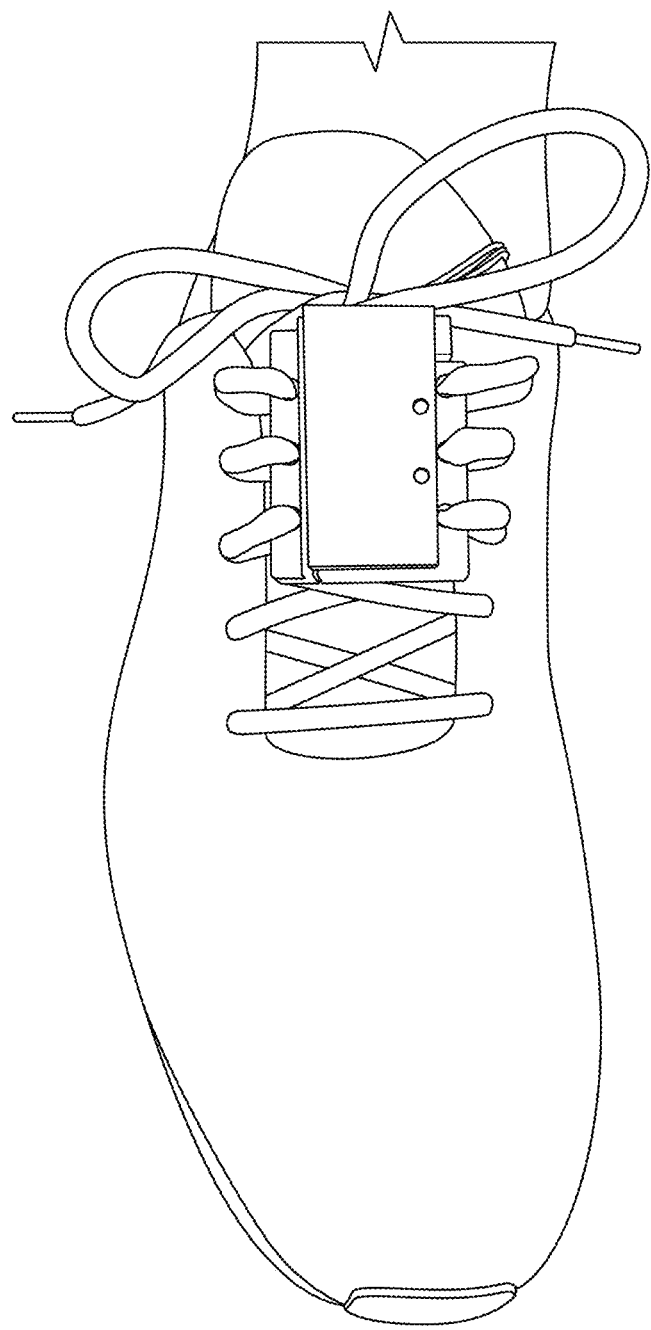
Figure 4D:
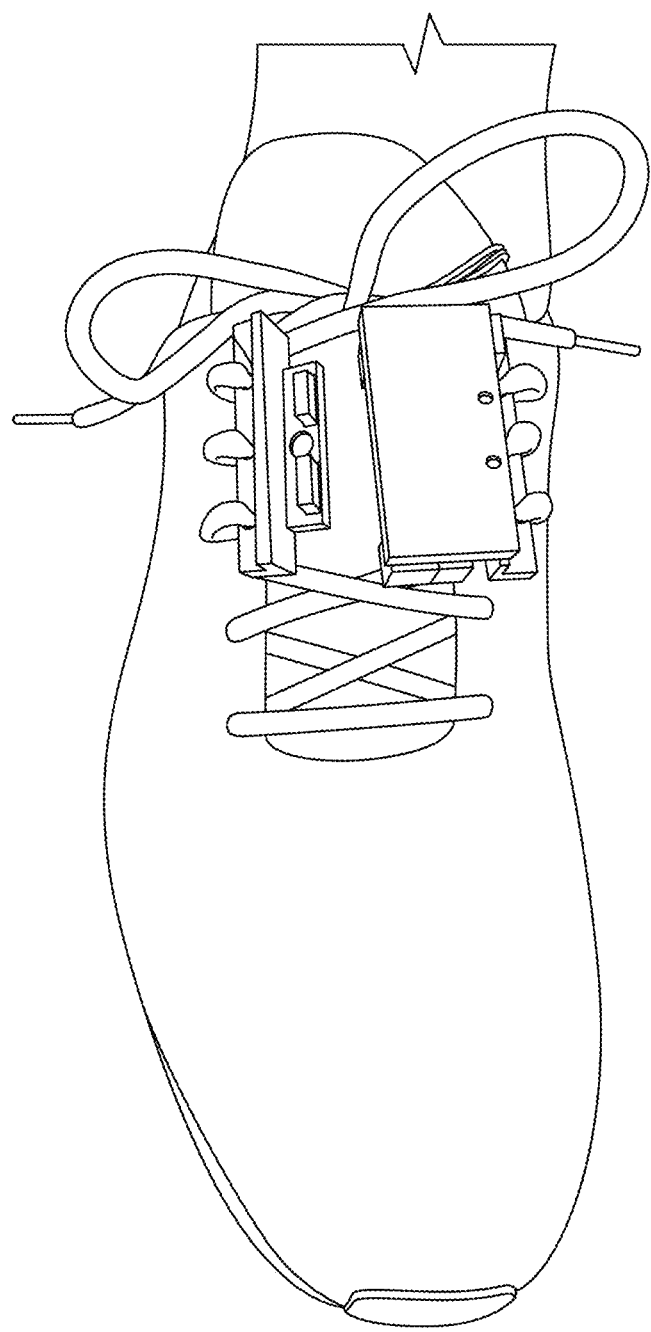

FIGS. 4A-4D are photographs of various views of a lace-tensioning system 103. FIG. 4A is a perspective view of an exemplary lace-tensioning system 103 in its locked position. Holes for attaching laces are visible on one side. FIG. 4B is a profile view of an exemplary lace-tensioning system 103 in its unlocked position. Holes for attaching laces are visible on one side of the disconnected piece. FIG. 4C is a photograph of an exemplary lace-tensioning system 103 in its locked position attached to the shoe. Holes in the lace-tensioning assemblies for attaching the laces of the shoe to the lace-tensioning system 103 are visible on both sides. FIG. 4D is a photograph of an exemplary lace-tensioning system 103 in its unlocked position attached to the shoe. Holes for attaching the laces of the shoe to the lace-tensioning assemblies lace-tensioning system are visible on both sides.

EXAMPLE

Figure 5:
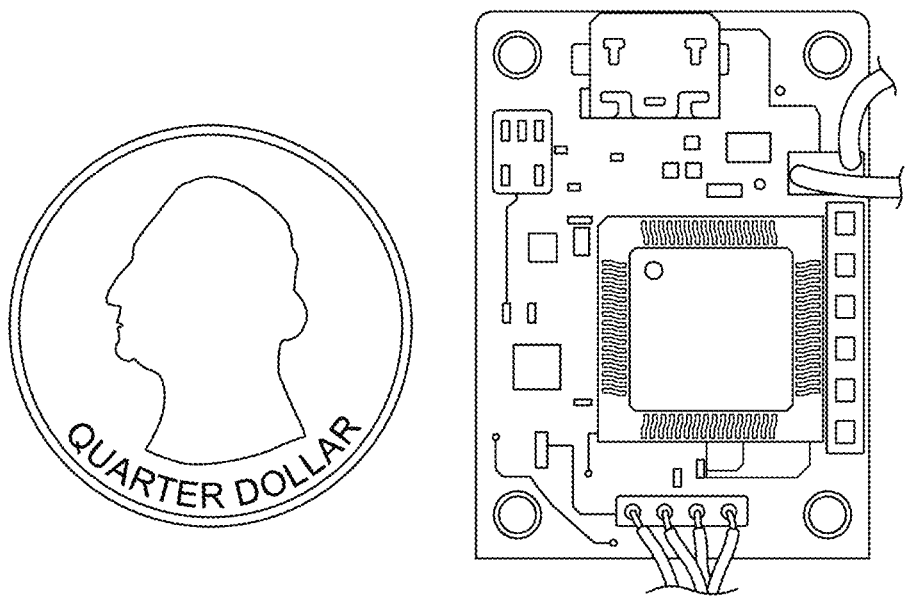
FIG. 5 is an image of a printed circuit board (PCB) of a non-limiting example of an exemplary lace-tensioning system for measuring motion of a shoe and lace tension of the shoe.
Figure 6:
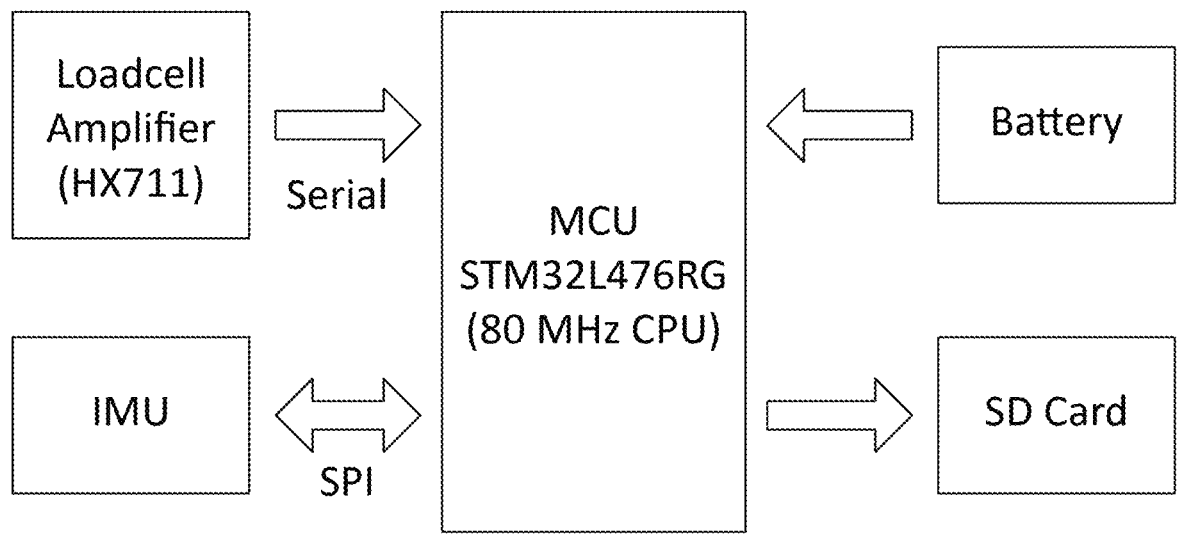
FIG. 6 is a block diagram of the exemplary IMU of FIG. 5's interfacings and data acquisition electronics.

Shown in FIG. 5 and described herein is one specific example of a lace-tensioning for measuring motion of a shoe and lace tension of the shoe. It is to be appreciated that the claims and embodiments described herein are not to be limited to this specific example. FIG. 5 is an image of a printed circuit board (PCB) of a non-limiting example of a lace-tensioning system for measuring motion of a shoe and lace tension of the shoe. In this example, the lace-tensioning system comprises a Mini Load Cell-500 g, Straight Bar (TAL221) and a 9-DOF Inertial Measurement Units (IMU) along with data acquisition electronics powered by a 3.7 V Li-polymer battery of 100 mAh capacity. This system also incorporated STM32L476RG, a Cortex-M4 Ultra-low-power ARM processor (ST Microelectronics, Geneva, Switzerland) with an 80 MHz CPU at 39 μA/MHz; a 32 GB micro-SD card to store data sampled at 512 Hz by the MCU (microcontroller); and a micro-USB interface to control data collection, access sensor signals stored in the SD card, update MCU timestamp, recharge the battery, and upload the firmware. A small 4-layer PCB (32 mm×24 mm) was design and manufactured to incorporate all electronics components of the system as shown in FIG. 5. The fully assembled PCB together with the battery weighs approximately 6 g. The mini loadcell was interfaced with the Microcontroller Unit (MCU) thorough HX711 (a precision 24-bit analog-to-digital converter) using serial interface. The motion tracking was performed by the IMUs (MPU-9250, InvenSense Inc., San Jose, Calif., USA), each combining a 3-axis gyroscope and a 3-axis accelerometer. The accelerometer and gyroscope of the module were configured to have a ±16 g and ±2000 dps measurement range, respectively, with 16 bits of resolution. The IMU was interfaced with the MCU through SPI interface. A block diagram of the exemplary IMU of FIG. 5 interfacings and data acquisition electronics is shown in FIG. 6.

EXPERIMENTAL PROCEDURE

Figure 7A:
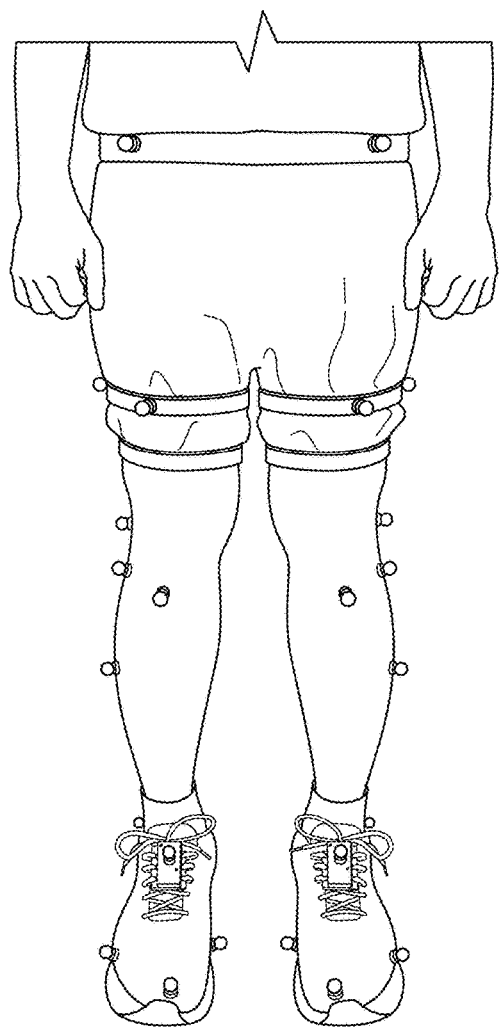
FIGS. 7A and 7B illustrate participants in a study of embodiments disclosed herein fitted with reflective markers and the exemplary lace-tensioning system.
Figure 7B:
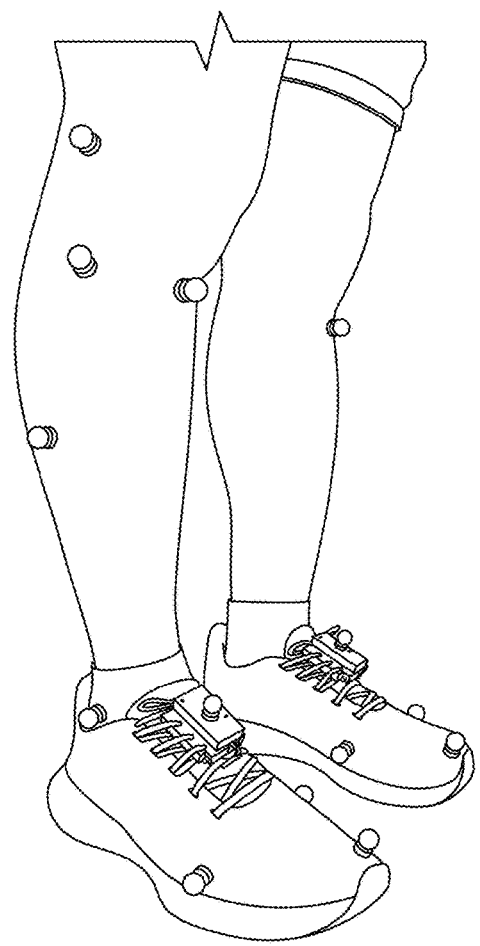

Ten healthy participants (Anthropometric Data summarized in Table 1, below) with no physical and cognitive abnormalities, participated in this study. Upon arrival to the laboratory, the investigative team thoroughly explained the informed consent document and clearly explained all study procedures. The protocol of the experiment was approved by the University of Alabama Institutional Review Board. Participants were asked to wear athletic clothing and running shoes and have their hair tied back out of the way. Then, they were fitted with reflective markers and the exemplary lace-tensioning system as shown in FIGS. 7A and 7B. Reflective markers were secured on subject skin/clothes using double-sided tape to record the motion with an infrared motion tracking system (Vicon Nexus and Vero infra-red Cameras, UK). The cameras were distributed all over the room to record the 3D position of the markers in the space without recording any subject feature.

TABLE 1

Anthropometric Data of the participants

| Subject | Gender | Age (year) | Weight (kg) | Height (cm) | Dominant leg | Shoe Type | Shoe Size (US) | Past Injuries |
|---|---|---|---|---|---|---|---|---|
| 1 | Male | 26 | 84 | 177.8 | Right | Running | 8.5 | None |
| 2 | Male | 30 | 64 | 175.25 | Right | Running | 8.5 | None |
| 3 | Male | 26 | 78 | 172.72 | Right | Running | 10 | None |
| 4 | Female | 30 | 55 | 169 | Right | Running | 8 | None |
| 5 | Male | 26 | 72 | 1.75.25 | Right | Running | 9 | None |
| 6 | Female | 27 | 84 | 167.64 | Right | Running | 8 | None |
| 7 | Male | 32 | 63.5 | 167.64 | Right | Running | 9 | None |
| 8 | Male | 25 | 61 | 162.56 | Right | Running | 8 | None |
| 9 | Male | 25 | 76 | 170.18 | Right | Running | 8.5 | None |
| 10 | Male | 28 | 68.5 | 167.64 | Right | Running | 9 | None |

Figure 8C:
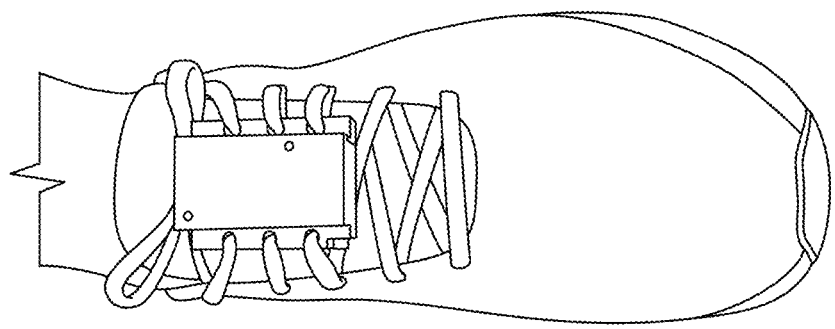
FIGS. 8A, 8B, and 8C illustrate two parts of an exemplary lace-tension system, which were separately mounted by routing the shoelace through the holes in the lace-tensioner assemblies, and then attached with each other through an embedded locking mechanism.
Figure 8B:
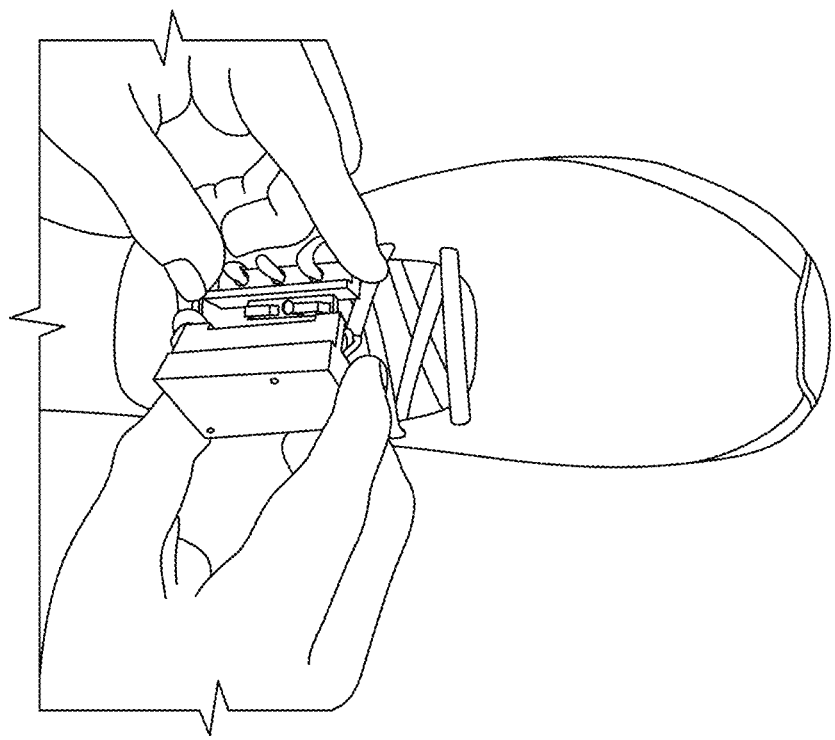
Figure 8A:
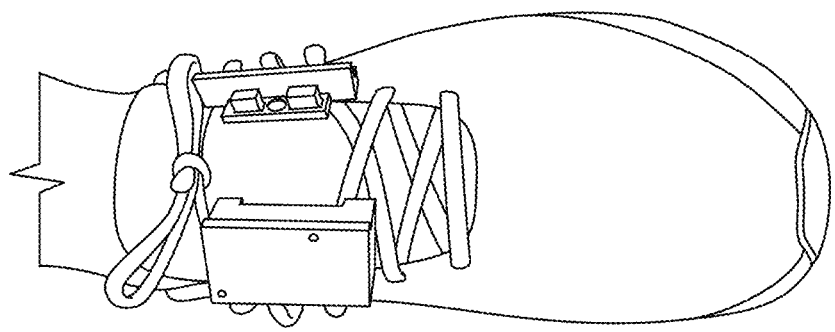
Figure 9A:
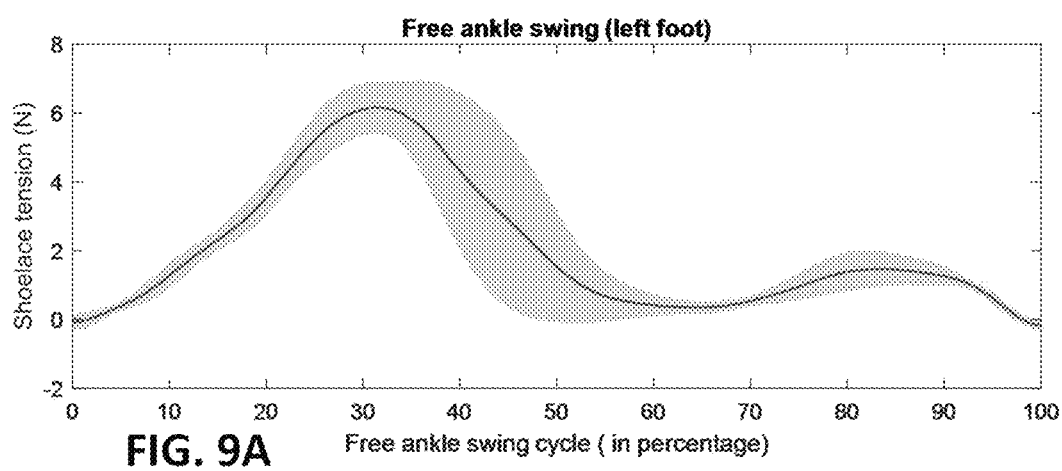
FIGS. 9A, 9B, 10A, and 10B illustrate the response of the exemplary lace-tensioning system's loadcell during free ankle swing of the left and right foot.
Figure 9B:
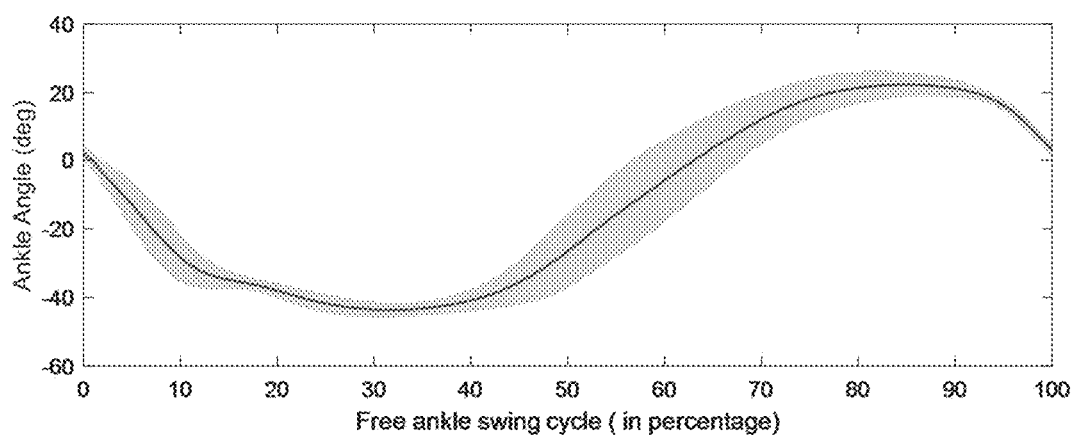
Figure 10A:
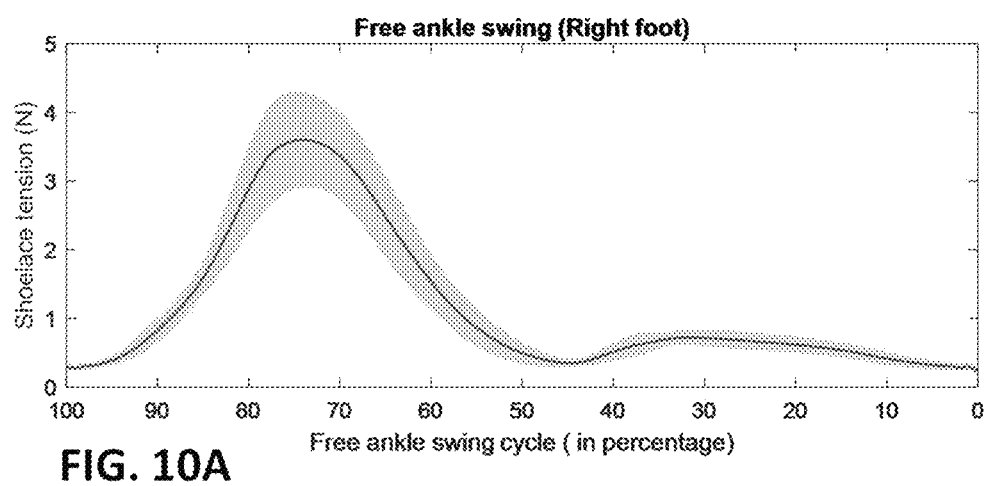
Figure 10B:
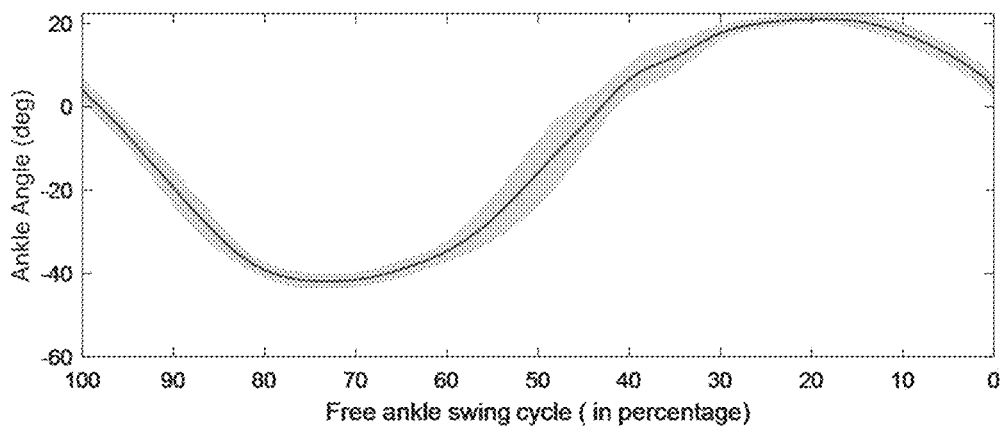

The exemplary system was fitted on the participant's shoes (left and right). The two lace-tensioner assemblies of the exemplary system were separately mounted by routing the shoelace through the holes in the assemblies, and then attached with each other through the embedded locking mechanism as shown in FIGS. 8A-8C. Little adjustments were performed to make it comfortable as well as to obtain the desired level of tightness. Once the laces were properly tensioned, the system was in locked state ready for testing.

In this exemplary study, four activities were performed: (A) Free ankle swing, (B) Weight shifting, (C) Sit-to-stand, and (D) Overground walking. Since, the tension of the shoelace changes due to the ankle movement and foot loading, to better understand their individual effect Free ankle swing (while no weight applied) and Weight shifting (while ankle joint remains stationary) activities were chosen for the experiment. Overground walking and sit-to-stand activities were chosen as they are most common in people's daily life, and involve significantly different limb/joint movements (small-range cyclical movements during walking, and big-range, transitional movements in sit-to-stand/stand-to-sit motion).The overground walking modality was completed at 3 gait speeds (slow, normal, and fast). The order of the four activities and the three-walking speed were randomized.

(A) Free ankle swing: During the free ankle swing condition, participants sat on a chair, raised their one foot parallel to ground and performed plantarflexion and dorsiflexion while keeping rest of the leg as stationary as possible. This activity was repeated for the other foot. Data were recorded for at least 20 plantarflexion and 20 dorsiflexion with the right foot and left foot (total 40 trials).

(B) Weight shifting: During the weight shifting condition, participants stood beside force plate and gradually shifted the weight on the force plate by keeping the ankle as stationary as possible. Data were recorded for at least 10 successful weight shifting on the force platform with the right foot and left foot (total of 20 trials). A successful trial was considered to be one in which the subject ankle joint movement was minimal or within a very small range (5 degree).

(C) Sit-to-stand: During the sit-to-stand condition, participants stood up on force plate from a chair and then sat down on the chair. The chair was positioned very close to the force plate so that person can easily stand up on the force plate. The sit-to-stand and stand-to-sit motion were repeated 10 times (20 in total).

(D) Overground walking: During the overground walking condition, participants walked up and down a 7-m walkway. A force platform (AMTI Accugait Optimized) was embedded in the middle of the walkway. Data were recorded for at least 5 successful strikes on the force platform with the right foot and left foot (total of 10 trials). A successful trial was considered to be one in which the subject did not make any noticeable alterations in stride length during the trial (i.e. no targeting) and contacts the force platform with the entire landing (left or right) foot. Overground walking was repeated for self-selected slow, normal, and fast speed. Familiarization trials were included to determine the optimal starting positions and starting foot to obtain successful trials for both the right and left feet. Subjects could rest at any time during the experiment if they feel tired.

In order to observe the effect of shoes, two participants use different shoes to repeat the experiments.

At the conclusion of each session, any of the used equipment were disposed of or cleaned (as applicable) with either an antibacterial microfiber towel or disinfectant spray. University Covid-19 guidelines and policies were followed throughout the entire process. The entire laboratory session was videotaped by an iON contour video camera at a 60 fps capture rate. In a smartphone application (aTimeLogger—Time Tracker), the start-end timestamp of each activity was marked. The Vicon system, video camera, and the smartphone were time-synchronized with the exemplary system by sending the same internet timestamp to all three systems.

Both the exemplary system and the eight-camera motion analysis system recorded the data simultaneously. The motion capture data were filtered a zero-phase lag fourth-order Butterworth low-pass filter with a 15 Hz cutoff frequency. The recorded system sensor signals were first processed by a dedicated MATLAB script for noise removal. A second-order low-pass Butterworth filter with an empirically selected cutoff frequency of 15 Hz was then applied to the sensor signals. Finally, processed lace-lock and camera motion data were averaged across all trials for each subject. The shoelace tension data was calibrated to zero position when the foot was relaxed and flat (meaning the ankle joint angle remains zero) on the ground while sitting on a chair with no weight applied.

The response of the exemplary system's loadcell during free ankle swing of the left and right foot are shown in FIGS. 9A, 9B, and 10A and 10B, respectively. Both sets of figures demonstrate an observable change in shoelace tension during ankle free swing motion and the shape of the trajectory is very consistent and repetitive over all the trials performed by the subjects. A major observation from the response is that the shoelace tension increases if the person intended to plantarflex or dorsiflex although the magnitude of the tension is higher for plantarflexion than the dorsiflexion. The loadcell response becomes maximum when maximum plantarflexion occurs.

Figure 11A:
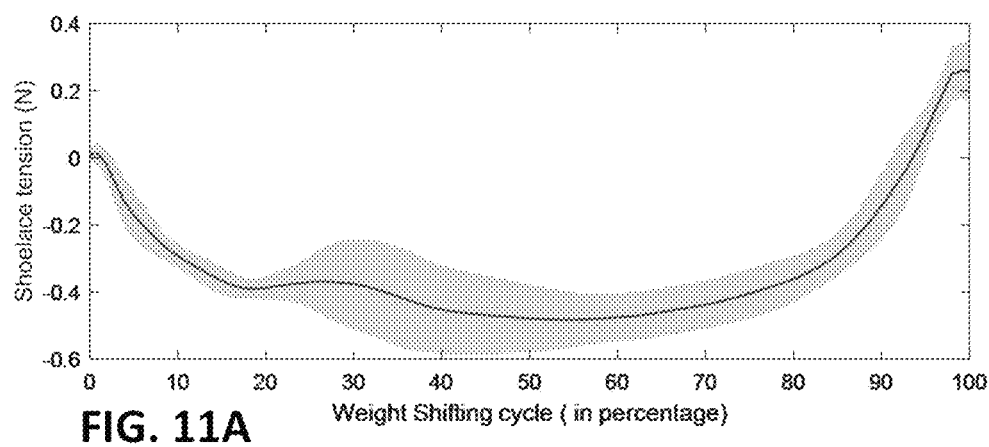
FIGS. 11A and 11B illustrate the response of the exemplary lace-tensioning system's loadcell during weight shifting conditions.
Figure 11B:
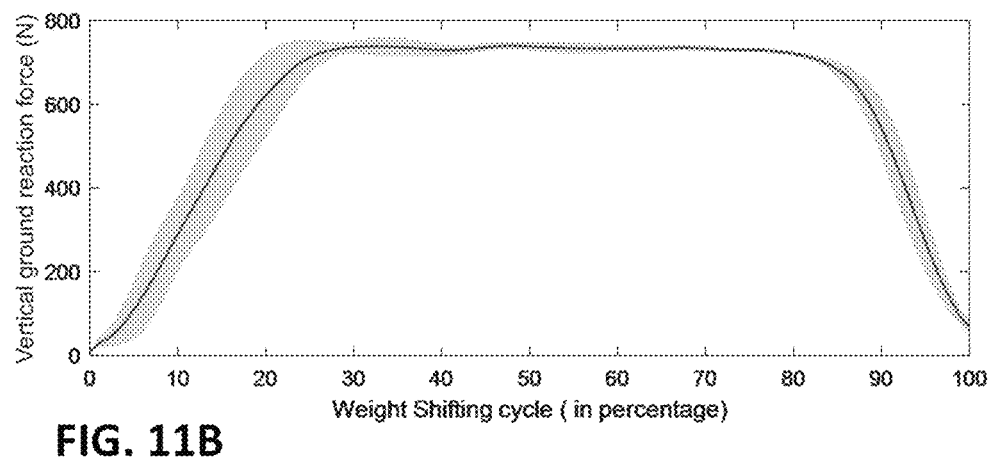

The response of the exemplary system's loadcell during weight shifting condition is shown in FIGS. 11A and 11B. This set of figures shows that the shoelace tension reduces with respect to gradual weight shifting and becomes minimum when full body weight is applied. As mentioned earlier, the shoelace tension was calibrated to zero when foot was flat with no weight applied hence the negative sign does not indicate the opposite direction of the tension rather it means the reduction of the tension from its initial state. It is also observed that there is no major change in the response when the person tries to stay still by applying total body weight. The shoelace tension increases when the person gradually withdraws the weight from the force plate.

Figure 12A:
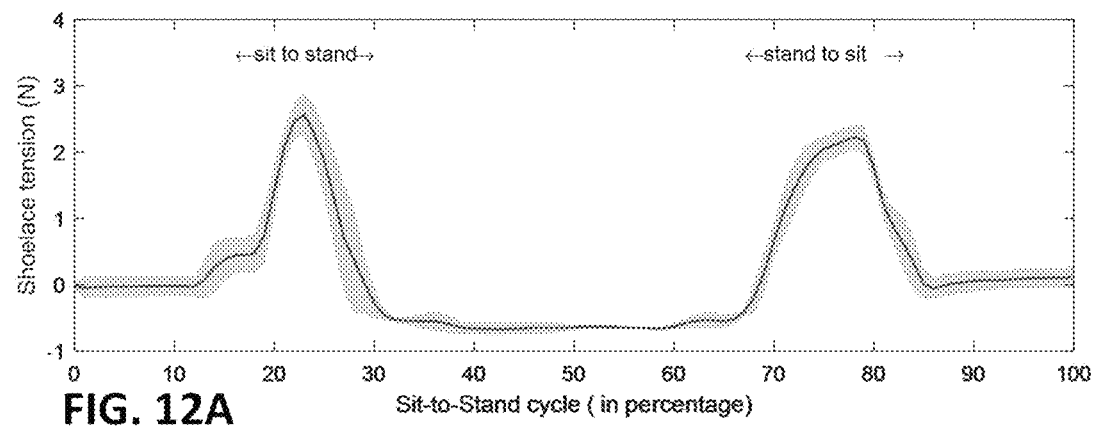
FIGS. 12A and 12B illustrate the response of the exemplary lace-tensioning system during sit-to-stand conditions.
Figure 12B:
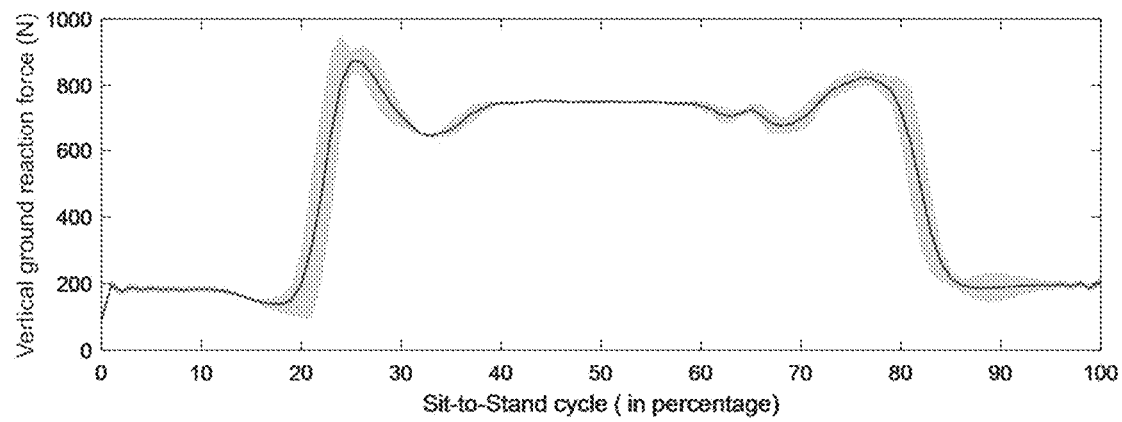

The response of the exemplary system during sit-to-stand condition is shown in FIGS. 12A and 12B. This set of figures demonstrates a specific shape of lace tension trajectory during sit-to-stand motion for all trials performed by the participants. By comparing the response with vertical ground reaction force, the loadcell response shows an early sign of the motion even before person starts to stand up by putting weight on the force plate. This information can be useful in sit-to-stand intent recognition (requires further validation). Similar to sit-to-stand, stand-to-sit shows a specific shape of the lace tension trajectory. It is also observable that during the standing part of the trajectory, lace tension becomes minimum which is clearly reflected by the sensor's loading condition response as described in the previous section.

Figure 13:
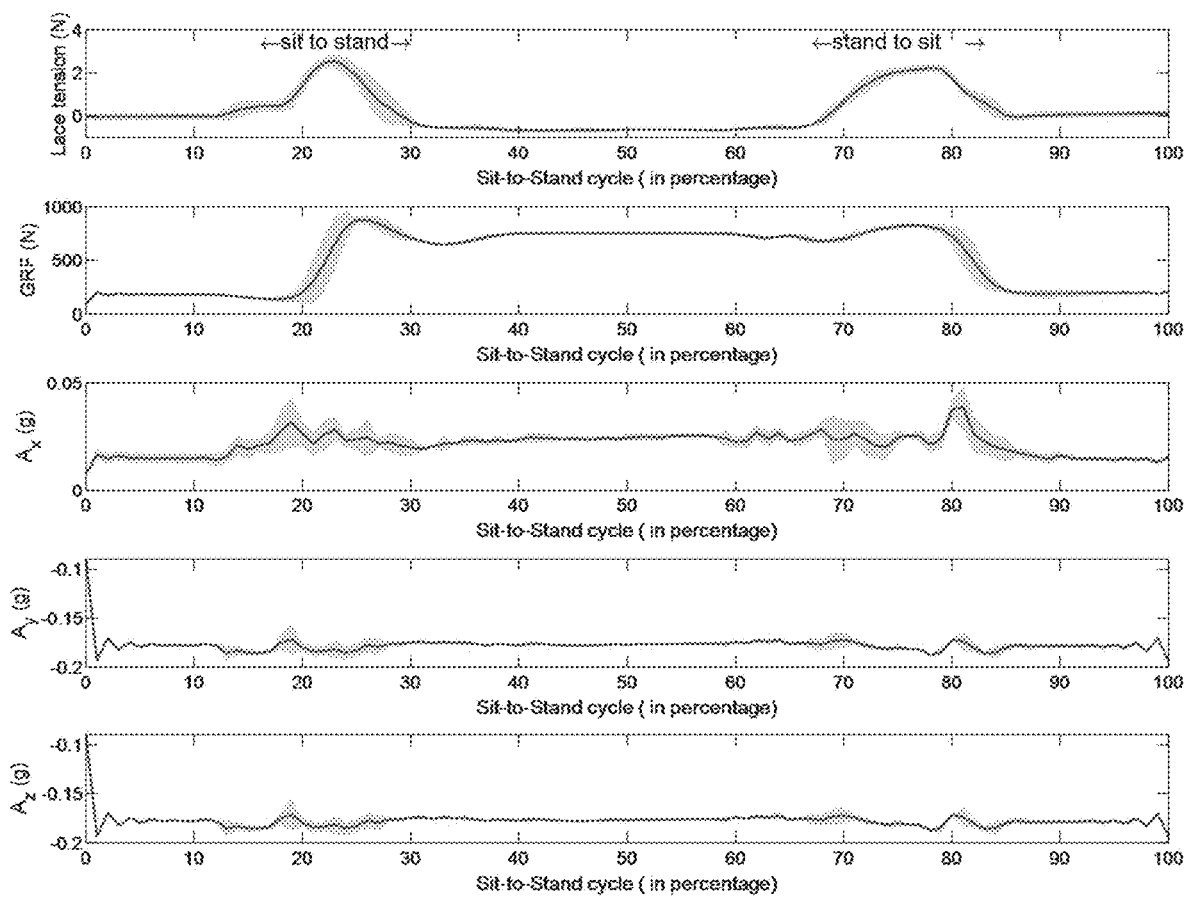
FIGS. 13 and 14 illustrates that the exemplary lace-tensioning system's IMU accelerometer and gyroscope responses compared against loadcell vertical ground reaction force during sit-to-stand and stand-to-sit motion.
Figure 14:
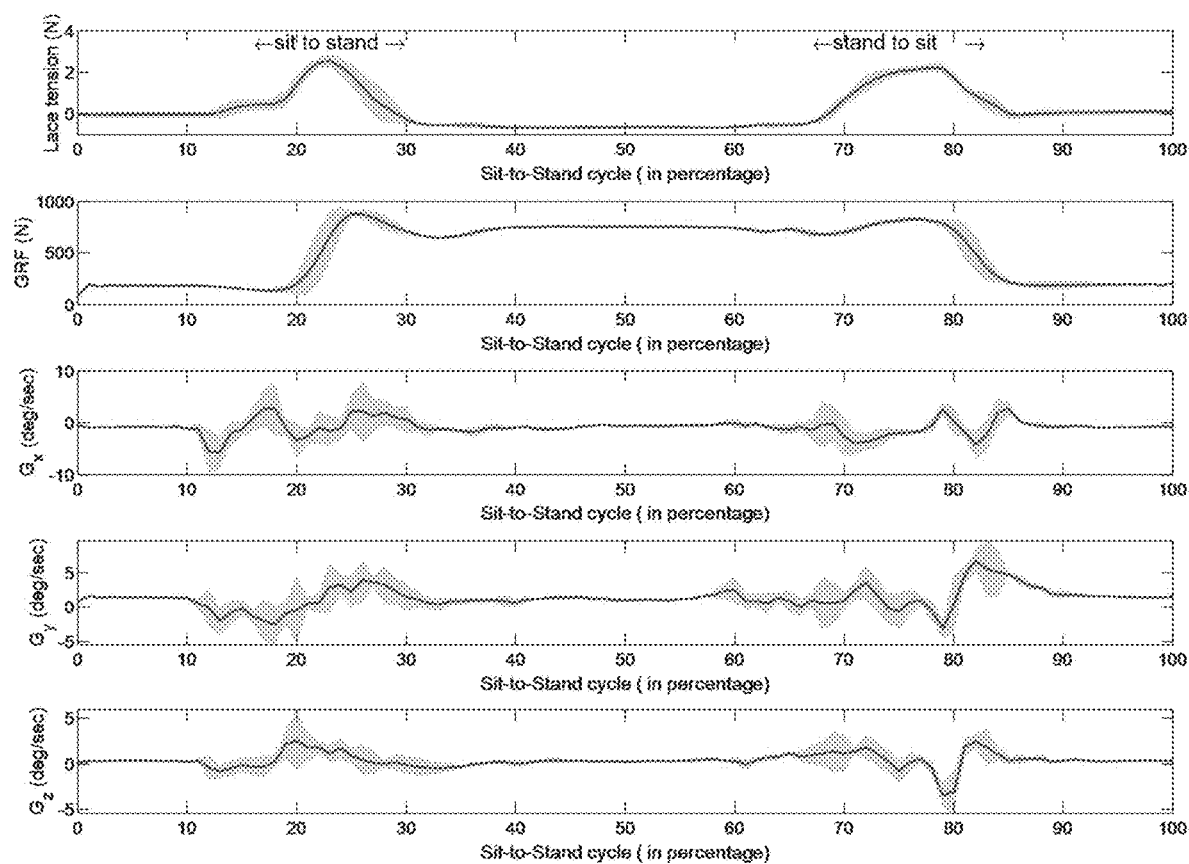

The exemplary system's IMU accelerometer and gyroscope responses are also compared against loadcell vertical ground reaction force during sit-to-stand and stand-to-sit motion as shown in FIGS. 13 and 14, respectively. The figures show that there are no distinguishable response from the accelerometer or the gyroscope during this testing.

Figure 15:
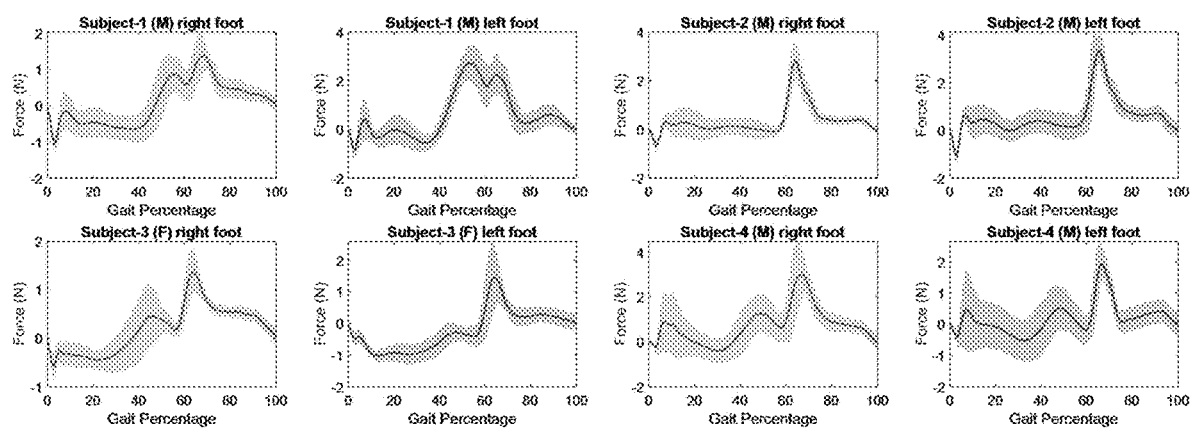
FIGS. 15 and 16 show the response of the exemplary lace-tensioning system during overground walking condition of different participants and the respective vertical ground reaction force trajectories.
Figure 16:
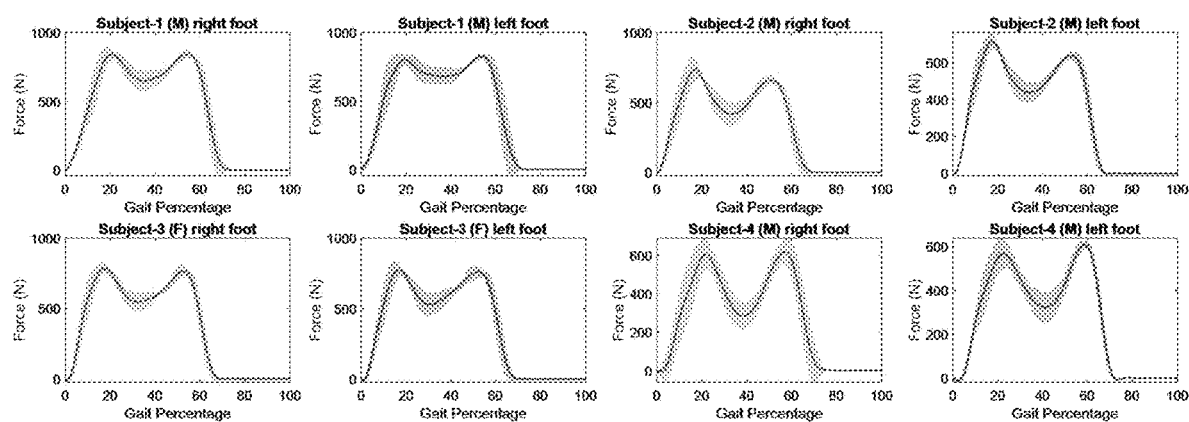

The response of the exemplary system during overground walking condition of different participants and the respective vertical ground reaction force trajectories are shown in FIGS. 15 and 16, respectively. FIG. 15 demonstrates that the shoelace tension trajectory maintains a very specific shape for each person during walking. The shape is consistent among both feet for all trials with different walking speeds. The figure also shows that the shapes of the lace tension trajectories are different for different participants but remains same for each person in all different trials which indicate that the exemplary system's sensor is able to distinguish different walking profile among different participants.

Figure 17A:
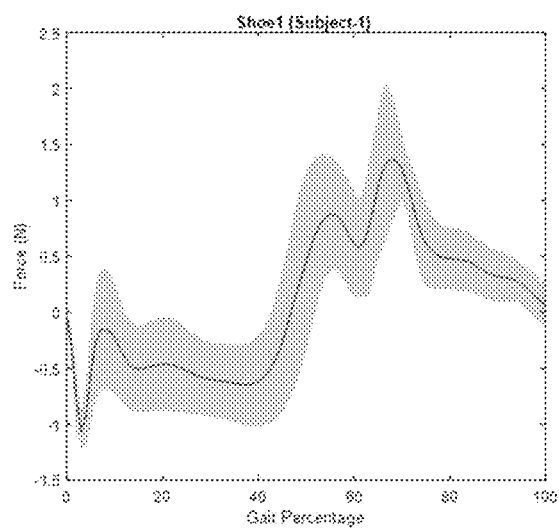
FIGS. 17A and 17B shows a comparison between shoe-lace tension trajectory during walking while the same person was wearing two different shoes.
Figure 17B:
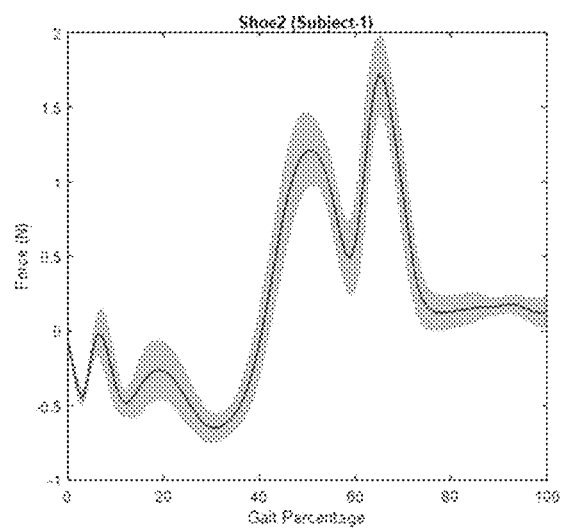

In order to observe the effect of different shoes on the exemplary system, participants used different shoes to repeat the experiments. FIGS. 17A and 17B shows a comparison between shoelace tension trajectory during walking while the same person was wearing two different shoes. Although the amplitudes of the trajectories are little different, but the shape remains similar for both shoes which further validates the exemplary system's ability to detect person's specific walking gait profile out any significant effect from the shoe.

Figure 18:
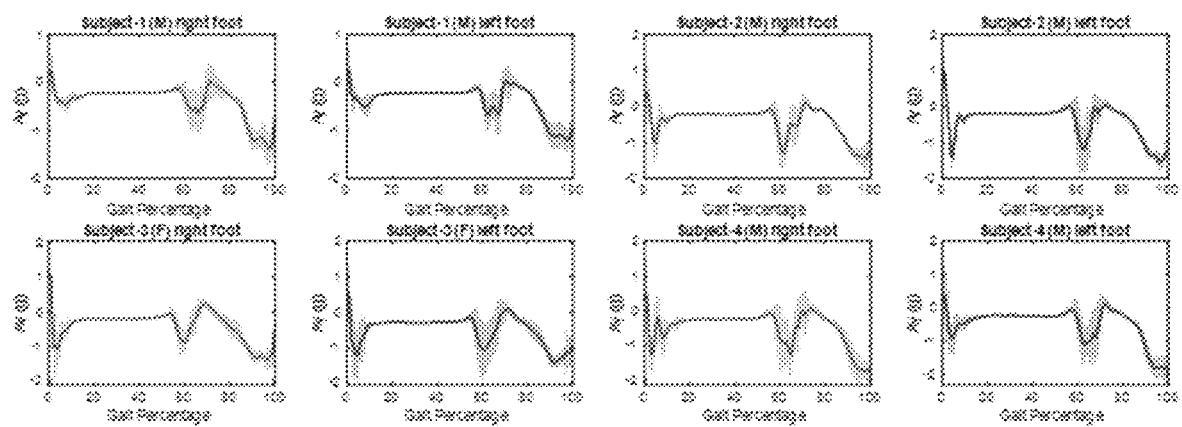
FIGS. 18, 19 and 20 show exemplary IMU accelerometer y and z-axis responses, and gyroscope x, responses of different subjects during walking, respectively.
Figure 19:
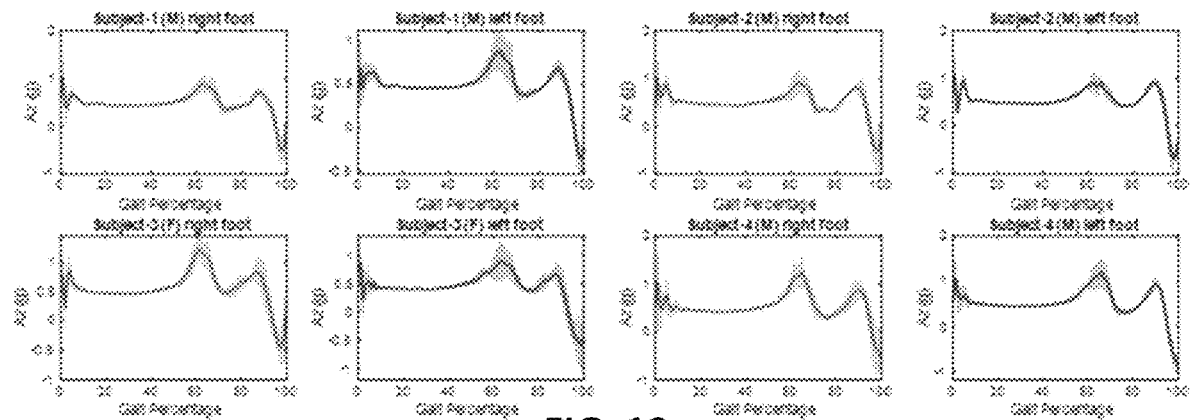
Figure 20:
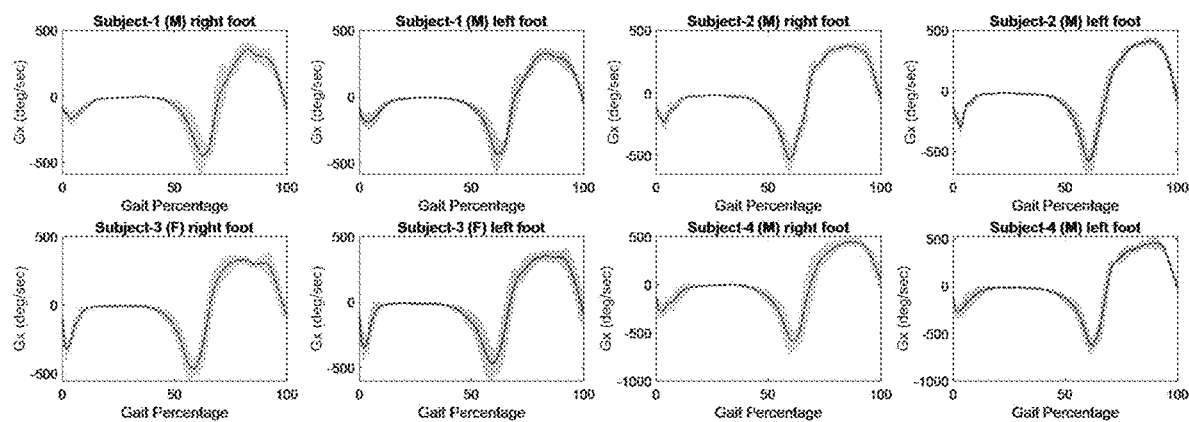

The IMU of the exemplary system measure the overall motion of the wearer's leg and foot during the walking cycle. The data collected from the IMU shows consistency among participants during different trials. The IMU accelerometer y and z-axis responses, and gyroscope x, responses of different subjects during walking are shown in FIGS. 18, 19 and 20, respectively.

RESULTS

Figure 21:
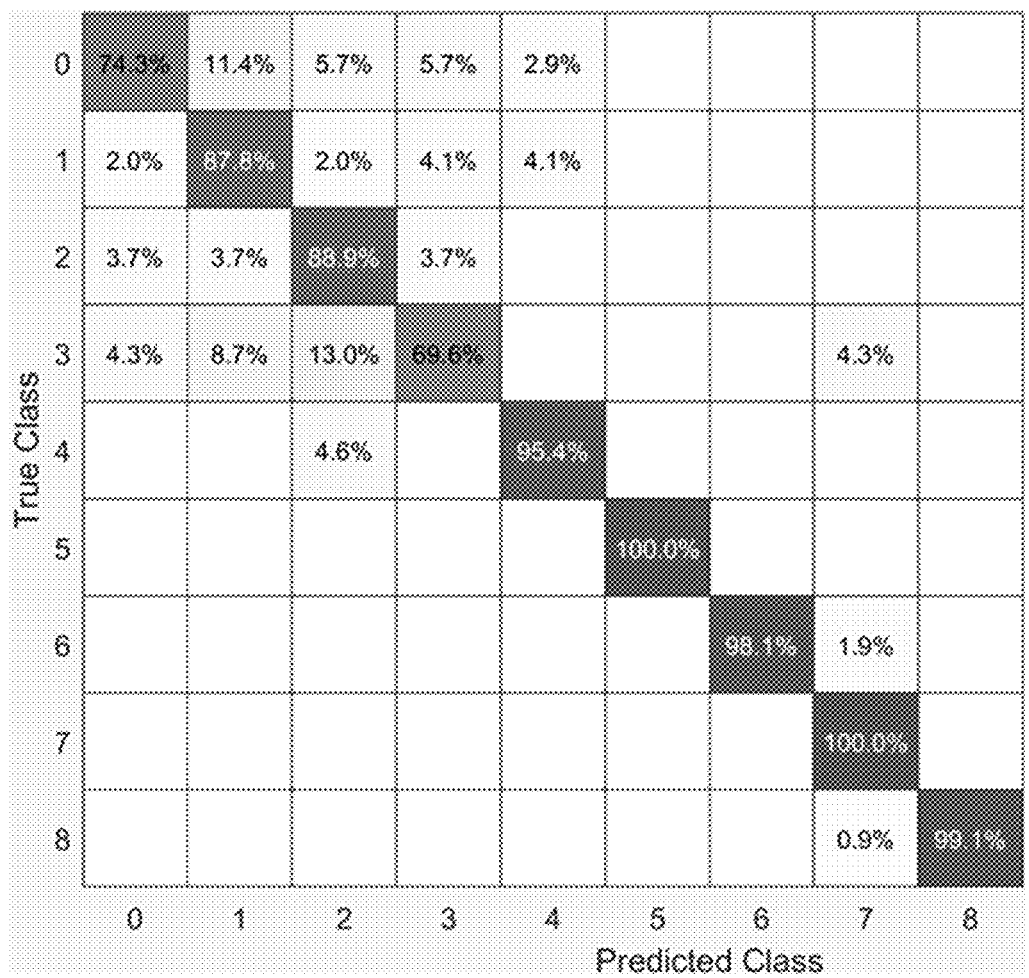
FIG. 21 is a graph showing that embodiments of the systems described herein are able to recognize nine classes of activities as compared to shoe-based monitors that do not include lace-tensioning that are only able to identify six classes of activities.

FIG. 21 is a graph showing that embodiments of the systems described herein are able to recognize at least nine classes of activities as compared to shoe-based monitors that do not include lace-tensioning that are only able to identify six classes of activities. As shown in FIG. 5, the activities are: 0—sitting; 1—standing; 2—sit to stand; 3—stand to sit; 4—walking; 5—running; 6—stair ascent; 7—stair descent; and 8—cycling. The embodiments described herein are currently able to identify these activities with an overall accuracy of approximately 94.8 percent.

CONCLUSION

It will be understood that each step of a method, block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. A method of measuring shoe motion and shoelace tension comprising:
   providing a shoe, said shoe comprising two parallel rows of eyelets configured to receive a single shoelace such that the shoelace can be used to apply tension to the shoe when said shoelace is threaded between said two parallel rows of eyelets and tightened;
   providing a lace-tensioning system for said shoe;
   measuring, using an inertia measurement unit (IMU) of the lace-tensioning system, mounted proximate a foot of a person, one or more parameters related to movement of the foot;
   measuring, using a lace-tensioning device of the lace-tensioning system, tension in the shoelace of the shoe when worn on the foot, wherein the lace-tensioning device comprises a female coupler, a male coupler, at least one force sensor connected between the female coupler and the male coupler that measures tension between the female coupler and the male coupler, and a plurality of lace-tensioner assemblies, wherein one or more of the plurality of lace-tensioner assemblies are connected to the female coupler and one or more of the plurality of lace-tensioner assemblies are connected to or the male coupler and the plurality of lace-tensioner assemblies are connected to the shoelace of the shoe such that the at least one force sensor measures tension in the shoelace of the shoe, said lace-tensioning device located between said two parallel rows of eyelets; and
   receiving, by a computing device in communication with the lace-tensioning system, the measured one or more parameters related to movement of the foot and the tension in the shoelace of the shoe worn on the foot, wherein the measured one or more parameters related to movement of the foot and the tension in the shoelace of the shoe worn on the foot are used by the computing device executing computer-readable instructions to make a determination about the person and/or communicate a message to the person.

2. The method of claim 1, wherein the IMU is incorporated into the lace-tensioning device, or wherein the IMU is separate from the lace-tensioning device.

3. The method of claim 1, wherein the IMU comprises one or more sensors, wherein the one or more sensors comprise one or more of an accelerometer, a gyroscope, a magnetometer, and a barometer.

4. The method of claim 1, wherein the at least one force sensor comprises a load cell.

5. The method of claim 1, wherein the one or more parameters relation to movement of the foot include one or more of an overall motion of the person's leg and foot during the leg's swing, motion of the foot when it is pushing off of a surface to obtain forward momentum in walking or running.

6. The method of claim 1, wherein the determination about the person includes one or more of a quality of a gait of the person, a strength of leg muscles of the person, an overall health of the person, a person's postures, physical activity and transitions between postures and activities, and measurements of quantifiable and qualitative characteristics of these postures, activities, and transitions.

7. The method of claim 6, wherein determining the overall health of the person includes identifying human activity mode, postures, and transitions between different activities/postures and/or estimating energy expenditure and/or quantifying rehabilitation outcomes of the person in real-world daily-living environments.

8. The method of claim 7, wherein identifying human activity modes, postures, and transitions between different activities/postures comprises identifiable activities and postures including but not limited to sitting, standing, sit to stand, stand to sit, walking, running, stair ascent, stair descent, and cycling.

9. The method of claim 6, wherein determining the quality of the gait of the person includes monitoring gait quality in daily life, detecting unexpected gait events, and estimating the risk of fall for frail older adults and individuals with neuromuscular pathologies, supporting the adaptive control of wearable assistive devices through the real-time measurement of healthy-side leg movements, and quantifying performance of athletes in sports.

10. The method of claim 1, wherein the message communicated to the person includes a message about a risk of fall.

11. A system for measuring activity modes of a person comprising:
a lace-tensioning system comprising at least an inertia measurement unit (IMU) and a lace tensioning device, said lace-tensioning device located between two parallel rows of eyelets of a shoe, said two parallel rows of eyelets configured to receive a single shoelace such that the shoelace can be used to apply tension to the shoe when said shoelace is threaded between said two parallel rows of eyelets and tightened,
wherein the IMU is mounted proximate a foot of a person, wherein the IMU measures one or more parameters related to movement of the foot, and
wherein the lace-tensioning device measures tension in a shoelace of a shoe worn on the foot, wherein the lace-tensioning device comprises a female coupler, a male coupler, at least one force sensor connected between the female coupler and the male coupler that measures tension between the female coupler and the male coupler, and a plurality of lace-tensioner assemblies, wherein one or more of the plurality of lace-tensioner assemblies are connected to the female coupler and one or more of the plurality of lace-tensioner assemblies are connected to or the male coupler and the plurality of lace-tensioner assemblies are connected to the shoelace of the shoe such that the at least one force sensor measures tension in the shoelace of the shoe; and
a computing device, wherein the computing device receives the measured one or more parameters related to movement of the foot and the tension in the shoelace of the shoe worn on the foot, wherein the measured one or more parameters related to movement of the foot and the tension in the shoelace of the shoe worn on the foot are used by the computing device executing computer-readable instructions to make a determination about the person and/or communicate a message to the person.

12. The system of claim 11, wherein the IMU is incorporated into the lace-tensioning device, or wherein IMU is separate from the lace-tensioning device.

13. The system of claim 11, wherein the IMU comprises one or more sensors, a processor in communication with the one or more sensors, and a transmitter, wherein the one or more sensors comprise one or more of an accelerometer, a gyroscope, a magnetometer, and a barometer.

14. The system of claim 11, wherein the at least one force sensor comprises a load cell.

15. The system of claim 11, wherein the one or more parameters relation to movement of the foot include one or more of an overall motion of the person's leg and foot during the leg's swing, motion of the foot when it is pushing off of a surface to obtain forward momentum in walking or running.

16. The system of claim 11, wherein the determination about the person includes one or more of a quality of a gait of the person, a strength of leg muscles of the person, and an overall health of the person, a person's postures, physical activity and transitions between postures and activities, and measurements of quantifiable and qualitative characteristics of these postures, activities, and transitions.

17. The system of claim 16, wherein determining the overall health of the person includes identifying human activity mode, postures, and transitions between different activities/postures and/or estimating energy expenditure and/or quantifying rehabilitation outcomes of the person in real-world daily-living environments.

18. The system of claim 16, wherein identifying human activity modes, postures, and transitions between different activities/postures comprises identifiable activities and postures including but not limited to sitting, standing, sit to stand, stand to sit, walking, running, stair ascent, stair descent, and cycling.

19. The system of claim 16, wherein determining the quality of the gait of the person includes monitoring gait quality in daily life, detecting unexpected gait events, estimating the risk of fall for frail older adults and individuals with neuromuscular pathologies, supporting the adaptive control of wearable assistive devices through the real-time measurement of healthy-side leg movements, and/or quantifying performance of athletes in sports.

20. The system of claim 11, wherein the message communicated to the person includes a message of a risk of fall.

21. A system for measuring tension in a shoelace, said system comprised of
a first assembly, said first assembly comprised of a first lace tensioner, a female coupler, wherein the first lace tensioner is attached to the shoelace;
an inertia measurement unit (IMU), wherein the IMU comprises one or more sensors, a processor in communication with the one or more sensors, and a transmitter, wherein the IMU measures one or more parameters related to movement of a foot;
a second assembly, said second assembly comprising a second lace tensioner and a male coupler, wherein the second lace tensioner is also attached to the shoelace such that tension in the shoelace pulls the first lace tensioner and the second lace tensioner in opposite directions; and
one or more force sensors, wherein at least one force sensor of the one or more force sensors is connected between the female coupler and to the male coupler such that the at least one force sensor measures tension in the shoelace of the shoe,
wherein said first assembly and said second assembly are located between two parallel rows of eyelets of a shoe, said two parallel rows of eyelets configured to receive the shoelace such that the shoelace can be used to apply tension to the shoe when said shoelace is threaded between said two parallel rows of eyelets and tightened.

22. The system of claim 21, wherein at least one of the force sensors comprises a load cell, and wherein the one or more sensors of the IMU comprise one or more of an accelerometer, a gyroscope, a magnetometer, and a barometer.

* * * * *